US010436759B2

(12) United States Patent
Mann, III et al.

(10) Patent No.: US 10,436,759 B2
(45) Date of Patent: Oct. 8, 2019

(54) METHODS AND APPARATUS TO MONITOR A CONDITION OF A STRUCTURE

(71) Applicant: FISHER CONTROLS INTERNATIONAL LLC, Marshalltown, IA (US)

(72) Inventors: Julian Adin Mann, III, Ames, IA (US); Jessica Dawn Myers, Arvada, CO (US)

(73) Assignee: Fisher Controls International LLC, Marshalltown, IA (US)

( * ) Notice: Subject to any disclaimer, the term of this patent is extended or adjusted under 35 U.S.C. 154(b) by 173 days.

(21) Appl. No.: 15/404,839

(22) Filed: Jan. 12, 2017

(65) Prior Publication Data
US 2018/0196014 A1 Jul. 12, 2018

(51) Int. Cl.
*G01N 29/44* (2006.01)
*G01N 29/46* (2006.01)
(Continued)

(52) U.S. Cl.
CPC ...... *G01N 29/4418* (2013.01); *G01M 5/0066* (2013.01); *G01N 29/12* (2013.01); *G01N 29/46* (2013.01); *G05B 23/024* (2013.01)

(58) Field of Classification Search
CPC .... G01N 29/4418; G01N 29/12; G01N 29/46; G01M 5/0066; G05B 23/024
See application file for complete search history.

(56) References Cited

U.S. PATENT DOCUMENTS

| 4,831,365 A * | 5/1989 | Thomas ............. G05B 19/4065 340/680 |
| 2014/0005960 A1 | 1/2014 | Anderson et al. |

(Continued)

OTHER PUBLICATIONS

Schallhorn and Rahmatalla, "Damage Detection of retrofitted crack re-initation and growth", Journal of Civil Structural Health Monitoring, Published online Apr. 29, 2015.*

(Continued)

*Primary Examiner* — Justin Seo
*Assistant Examiner* — John M Royston
(74) *Attorney, Agent, or Firm* — Hanley, Flight & Zimmerman, LLC

(57) ABSTRACT

Methods, apparatus, and articles of manufacture to monitor a condition of a structure are disclosed. An example apparatus includes an operational collection engine to measure first operational acceleration information from a first sensor installed at a first location and second operational acceleration information from a second sensor installed at a second location on a structure, a first vibration model response calculator to calculate a first vibration model response by entering the measured first and second operational acceleration information into a first vibration model, a second vibration model response calculator to calculate a second vibration model response by entering a calculated number of operational cycles into a second vibration model, a deviation threshold analyzer to determine a difference between the first vibration model response and the second vibration model response and an alert generator to generate an alert to identify a condition of the structure based on the difference between the first vibration model response and the second vibration model response.

20 Claims, 14 Drawing Sheets

(51) Int. Cl.
  *G01N 29/12* (2006.01)
  *G01M 5/00* (2006.01)
  *G05B 23/02* (2006.01)

(56) References Cited

U.S. PATENT DOCUMENTS

2016/0258836 A1\* 9/2016 Raman ................ G01M 5/0066
2018/0130489 A1\* 5/2018 Cheng ................ B23Q 17/0976

OTHER PUBLICATIONS

International Searching Authority, "Written Opinion," issued in connection with application No. PCT/US2018/012016 dated May 24, 2018, 6 pages.

International Searching Authority, "Search Report," issued in connection with application No. PCT/US2018/012016 dated May 24, 2018, 6 pages.

Schallhorn Charles et al., "Damage detection of retrofitted crack reinitiation and growth," Journal of Civil Structural Health Monitoring, Springer Berlin Heidelberg, vol. 5, No. 4, Apr. 29, 2015, pp. 377-388, abstract only provided, 11 pages.

Yun Lai Zhou, "Structural Health Monitoring by Using Transmissibility," Madrid, Spain, 2015, 155 pages.

\* cited by examiner

METHODS AND APPARATUS TO MONITOR A CONDITION OF A STRUCTURE

FIELD OF THE DISCLOSURE

This disclosure relates generally to process control systems and, more particularly, to methods and apparatus to monitor a condition of a structure.

BACKGROUND

In recent years, process control systems, like those used in chemical, petroleum, and/or other processes, have grown progressively more complex with the proliferation of newer and more powerful controllers. Current generation process control systems include a greater number and variety of field devices or instruments for measuring and/or controlling different aspects of a process environment. In addition to utilizing field devices to monitor and/or control core processes, field devices have been increasingly used for peripheral tasks such as prognostic health monitoring.

Process control systems in which field devices fail during operation can experience increased periods of downtime. Field device failure during operation can also create hazardous operating conditions if the failed field devices provide erroneous or inaccurate data to the process control system. Failed field devices that provide electronic feedback (e.g., pressure transducers, temperature transducers, etc.) to controllers can be mitigated by performing a controlled shut down of the process equipment or by bypassing the input of the failed field devices to corresponding controller algorithms. However, failed field devices that do not provide electronic feedback (e.g., hydraulic actuators, pneumatic valves, etc.) during operation may not alert the controller that there is a problem and may lead. process control systems to function in an unknown, unstable and/or unsafe modes of operation.

Devices within the process control system may also be located in difficult environments such as areas with extreme vibration, high pressure, and/or wide temperature ranges that may cause accelerated failure. With the implementation of increasingly powerful controllers, process control systems can utilize additional sensors to monitor field devices in these difficult environments. Monitoring field devices using additional sensors and peripheral algorithmic routines can be used to predict potential failures and enable technicians to replace the potentially faulty field devices during periodic maintenance as opposed to stopping operation of the system to replace field devices.

SUMMARY

An example apparatus disclosed herein includes an operational collection engine to measure first operational acceleration information from a first sensor installed at a first location and second operational acceleration information from a second sensor installed at a second location on a structure. The example apparatus also includes a first vibration model response calculator to calculate a first vibration model response, a second vibration model response calculator to calculate a second vibration model response, a difference calculator to determine a difference between the first and second vibration model response and an alert generator to generate an alert to identify a condition of the structure based on the difference between the first and second vibration model response.

An example method disclosed herein includes measuring first operational acceleration information from a first sensor installed at a first location and second operational acceleration information from a second sensor installed at a second location on a structure. The example method also includes calculating a first vibration model response, calculating a second vibration model response, calculating a difference between the first and second vibration model response and identifying a condition of the structure based on the difference between the first and second vibration model response.

An example tangible computer-readable storage disk or storage device includes instructions, which when executed, cause a machine to at least measure first operational acceleration information from a first sensor installed at a first location and second operational acceleration information from a second sensor installed at a second location on a structure, calculate a first vibration model response, calculate a second vibration model response, determine a difference between the first and second vibration model response and identify a condition of the structure based on the difference between the first and second vibration model response.

BRIEF DESCRIPTION OF THE DRAWINGS

Wherever possible, the same reference numbers will be used throughout the drawings) and accompanying written description to refer to the same or like parts.

DETAILED DESCRIPTION

Figure 1:
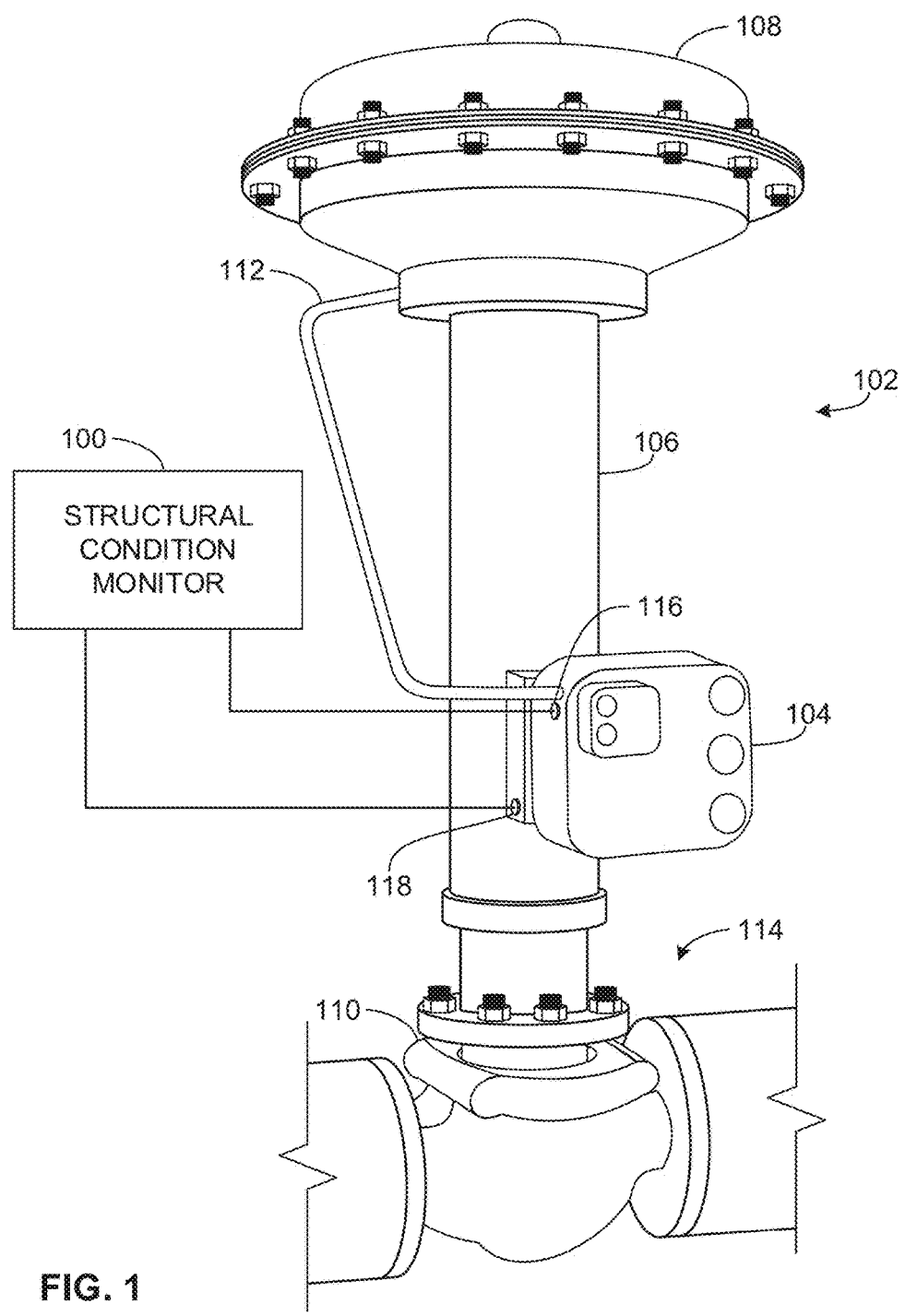
FIG. 1 is a schematic illustration of an example structural condition monitor apparatus in accordance with the teachings of this disclosure.

Process control systems are growing increasingly complex as individual components with increased data acquisition resolution, processing power and signal conditioning are developed. Process control systems are used to monitor and/or control different aspects of an operation to be conducted in a process environment, such as, for example, manufacturing components, processing raw chemical materials, etc. Process control systems typically contain at least one controller with accompanying inputs and outputs, allowing the controller(s) to acquire signals from various input field devices and/or instruments and control various output field devices and/or instruments.

Field devices or instruments (e.g., control devices), such as, for example, sensors, switches, transmitters, valve controllers, etc. are used throughout a process control system to measure and control different aspects (e.g., other process control devices) of the process control system. As used herein, field devices, instruments and/or sensors may be used interchangeably. Field devices used as inputs for a process control system may be, for example, feedback position sensors, pressure transducers, temperature transducers, etc. that are used to continuously monitor various metrics of the process environment. Field devices used as outputs for a process control system may be, for example signal conditioners, switches, solenoids, etc. to perform various control actions when induced by the controller.

The above described field devices operate in a wide variety of environments such as, for example, inside a temperature-controlled plant, outside in sub-Sahara Africa, etc. Difficult operational environments for field devices may also exist within the process environment itself, such as, for example, inside process environment zones that experience extreme temperature variations, vibration, etc. Difficult operational environments may cause a field device to undergo accelerated wear and greatly reduce the expected lifetime of the field device. For example, a field device that is installed in process piping connected downstream from a positive-displacement pump may experience extreme vibration during operation. In the illustrated example, individual components of the field device such as, for example, components that are chemically installed (e.g., affixed to a surface with an adhesive) and/or mechanically installed (e.g., screwed into place, welded together, etc.) may become dislodged due to the extreme vibration in a shorter period of time than a field device not experiencing the same extreme vibration.

Field device failures can result from a multitude of causes such as, for example, environmental factors, manufacturing defects, typical operation, etc. However, the timing of a failure may not be predictable and may occur during operation. Not knowing when a field device is expected to fail or about to reach a condition of impending failure poses a significant problem to the continuous operation of existing process control systems. A sudden field device failure during operation may result in the loss of the field device and equipment that the field device was monitoring and/or controlling. For example, failure of a pressure transducer installed in a valve seat in a positive-displacement pump may result in the report of an erroneous or incorrect value to the process control system controller, which may cause the pump to be unintentionally over pressured and damaged. In another example, if the positive-displacement pump fails independently of a field device during operation, the amount of downtime may be significantly greater to replace the pump as opposed to replacing the field device monitoring the pump. The remote location of some process control systems and process environments may, for example, compound the consequences of a field device failure due to increased downtime to gain access or travel to the area of the field device failure.

To overcome this problem of unexpected field device failure, some known systems use controllers that employ classification systems to predict expected failure timelines for field devices. For example, a controller may receive inputs such as measured process parameters (e.g., process pressure, process temperature, number of operating cycles, etc.) along with specific information related to the field device (e.g., make, model, operating characteristics, etc.) into a classification system to determine a predicted time-to-failure metric, which may then be used to initiate field device replacement. Other systems track operating hours and use periodic maintenance intervals to initiate replacement of field devices prior to failure. However, utilizing the above-described systems may increase equipment and labor costs by replacing field devices too early in their lifecycles or miss a potential failure before a scheduled maintenance. As a result, a field device with a significant amount of operating lifetime remaining may be prematurely replaced within such systems.

Example structural condition monitor apparatus disclosed herein relate to process control systems and, more specifically, to monitoring a condition of a structure. In general, the example structural condition monitor apparatus disclosed herein utilizes sensing devices such as, for example, sensors (e.g., acceleration sensors, motion sensors, vibration sensors, etc.) affixed to a structure of interest (e.g., a positive-displacement pump, a process control valve etc.) to acquire acceleration data and/or information to monitor the condition of the structure (e.g., the formation of a crack, the degradation of performance, etc.). As used herein, the terms "acceleration information," "motion information" and/or "vibration information" may be used interchangeably. Example sensors may also be affixed to locations on the structure of interest that may experience different vibration profiles. For example, a pneumatically actuated butterfly valve may be connected via flanges to process piping downstream of a positive-displacement pump. The butterfly valve may have at least one sensor affixed in proximity to a pneumatic connection and at least one sensor installed on the body of the butterfly valve. Example sensors may also be affixed to a structure that is a source of vibration (e.g., a centrifugal pump, a positive-displacement pump, etc.) or located near the source of the vibration (e.g., affixed to process piping connected downstream from a positive-displacement pump, etc.) experienced by the structure of interest. For example, a hydraulic process control valve connected via flanges to process piping downstream from a positive-displacement hydraulic pump may have at least one sensor affixed on the body of the hydraulic process control valve while having at least one sensor installed on the body of the hydraulic pump.

In some example structural condition monitor apparatus disclosed herein, the above-described sensing devices (e.g., acceleration sensors, motion sensors, vibration sensors, etc.) may be coupled to a process control system via a controller for data acquisition and processing. In such disclosed examples, the controller acquires and/or obtains acceleration information from at least one acceleration sensor during operation and processes the acquired acceleration information. For example, the controller may process the obtained acceleration information by entering the obtained acceleration information into a first vibration model and a second vibration model. In the illustrated example, an output of the first vibration model may be compared to an output of the second vibration model. The comparison between the outputs of the first and second vibration models may yield a difference. The controller may employ the difference to determine if the difference satisfies a threshold (e.g., the difference is greater than 1 Hz). In some disclosed instances, the controller may generate an alarm and/or alert message, in response to the difference satisfying the threshold, indicating the condition of the structure may be present.

In some example structural condition monitor apparatus disclosed herein, the first and second vibration models are derived by obtaining baseline acceleration information from at least one sensing device (e.g., at least one acceleration sensing device, at least one motion sensing device, at least one vibration sensing device, etc.) during one or more operating cycles and/or processes for a structure. As disclosed herein, the terms "acceleration sensing device," "acceleration sensor," "motion sensing device," "motion sensor," "vibration sensing device" and "vibration sensor" are used interchangeably. For example, the controller may obtain acceleration information from at least one acceleration sensor affixed to a control valve processing a baseline fluid (e.g., water). The baseline fluid may be processed by an actuator opening and closing the control valve under pressure for a fixed number of cycles. The obtained acceleration information may be used by the controller to calculate a transmissibility of the structure. In some examples disclosed herein, the transmissibility of the structure is defined as a ratio of an output response (e.g., an output acceleration response) and an input response (e.g., an input acceleration response). For example, the transmissibility of the structure may be the ratio of a first acceleration response obtained by a first acceleration sensor on the structure (e.g., the output response) to a second acceleration response obtained by a second acceleration sensor (e.g., the input response). As disclosed herein, the term "response" refers to a data subset of acceleration information collected during a defined time interval or during a time period in which an event occurs. As disclosed herein, the terms "acceleration response," "motion response" and/or "vibration response" are used interchangeably. For example, the acceleration response may be the acceleration information collected during a periodic time interval (e.g., every 100 milliseconds) and/or the acceleration information collected during a time period in which an event occurs such as, for example, the actuator 108 moving from an open position to a closed position, the valve 110 moving from an open position to a closed position, etc.

In some examples, the controller may generate the first vibration model for the structure. The controller may be configured to generate the first vibration model for the structure by performing a curve fit for calculated transmissibility information. Generating the first vibration model may include, for example, the controller calculating the transmissibility of the structure for a range of measured frequencies by one or more field devices. The controller may identify a frequency at which resonance occurs, or herein referred to as the frequency at which the maximum transmissibility occurs. The controller may calculate initial values for variables in one or more known transmissibility characteristic equations. Such transmissibility variables may include, for example, an amplitude, a bandwidth, a damping ratio, a half power frequency, a natural frequency, a quality factor, a transmissibility, a vertical shift, etc. The controller may also optimize the transmissibility variables using one or more processes such as, for example, a sum of squared errors prediction (SSE) process, a least squares process, a mean squared error process, etc.

In some examples, the controller processes the obtained acceleration information to identify one or more data outliers. For a selected acceleration response of interest, the controller may calculate an average value for one or more transmissibility variables over range of measured frequencies. For a selected frequency, the controller may determine a difference between a calculated transmissibility variable value and the calculated average transmissibility variable value. The controller may identify data outliers by determining if the difference satisfies a threshold (e.g., the difference exceeds a threshold of one standard deviation). The controller may eliminate the identified data outlier(s) and/or eliminate a set of data based on the identified data outlier(s).

In some examples, the controller may generate the second vibration model for the structure. The controller may be configured to generate the second vibration model for the structure by performing a curve fit for calculated natural frequency information. Generating the second vibration model may include, for example, the controller calculating a natural frequency of the structure during a number of operating cycles. The controller may calculate an average natural frequency for the number of operating cycles. For each operating cycle, the controller may calculate a difference between the calculated natural frequency of the operating cycle and the calculated average natural frequency for the number of operating cycles. The controller may also calculate the sum of the calculated differences and calculate an average of the sum of calculated differences. In some examples, the controller may generate values for one or more variables in a linear fit model such as, for example, a slope and a y-intercept. For example, the controller may calculate the slope as a ratio of the calculated average difference and the number of operating cycles. In some examples, the controller may identify the y-intercept of the linear fit model as the calculated average natural frequency for the number of operating cycles.

In some examples, the controller may compare the output of the first and second vibration models. For example, the controller may enter obtained acceleration information into the first vibration model to calculate a first natural frequency. The controller may also enter the obtained acceleration information into the second vibration model to calculate a second natural frequency. The controller may determine a difference between the first and second calculated natural frequencies as calculated by the first and second vibration models. In some examples, the controller may generate an alert if the difference satisfies a threshold (e.g., the difference is greater than 1 Hz). Such alerts may be, for example, sounding an alarm, propagating an alert in a process control network, generating an alert report etc.

In some disclosed examples, the controller may not generate a plurality of vibration models for the structure. For example, the controller may obtain acceleration information from one or more acceleration sensors during one or more operating cycles of the structure. The controller may calculate a natural frequency of the structure for each operating cycle and calculate an average natural frequency for the one or more operating cycles. The controller may generate a natural frequency model as described above by calculating at least the slope and y-intercept of a linear fit model. In some examples, the controller may obtain acceleration information for additional operating cycles and calculate the natural frequency of the structure for the additional operating cycles. For each operating cycle, the controller may (1) calculate a difference between the calculated natural frequency of the structure and the calculated average natural frequency and/or (2) calculate a difference between the calculated natural frequency of the structure and the calculated natural frequency from the generated natural frequency model. The controller may generate an alert in response to either or both differences satisfying a threshold (e.g., the difference is greater than 1 Hz).

Turning to FIG. 1, an example structural condition monitor apparatus 100 disclosed herein operates in a process control environment 102 by monitoring a condition of a structure of a field device 104 (e.g., an electronic valve controller). In the illustrated example, the field device 104 is an electronic valve controller housed in an enclosure and is coupled to an example pneumatically actuated valve assembly 106 that includes at least an actuator 108 and a valve 110 (e.g., a butterfly valve, a gate valve, etc.). However, other valve assemblies may additionally or alternatively be utilized, such as an electrically actuated valve assembly, a hydraulically actuated valve assembly, etc. The field device 104 measures one or more parameters of the actuator 108 and/or the valve 110 (e.g., the position of the valve) and/or controls one or more parameters of the actuator 108 and/or the valve 110. The field device 104 includes a connection point for a pneumatic tube connection 112. The field device 104 enables pneumatic control of the actuator 108 via the pneumatic tube connection 112.

In the illustrated example, the valve assembly 106 is installed in a fluid process system 114 (e.g., a distribution piping system) of a plant environment or processing system. The fluid process system 114 may be located in an environment that may expose the field device 104 and/or valve assembly 106 to at least one difficult operating condition (e.g., extreme vibration, a wide temperature range, etc.) and cause premature failure of the field. device 104 due to accelerated wear. For example, the field device 104 and the valve assembly 106 may be installed downstream of a positive-displacement pump. Different failure modes of the field device 104 may occur due to accelerated wear such as, for example, the pneumatic tube connection 112 decoupling from the field device 104, components inside the field device 104 decoupling from the electronic valve controller, etc.

In the illustrated example of FIG. 1, there is a first vibration sensing device 116 (e.g., an acceleration sensor, a motion sensor, a vibration sensor, etc.) affixed to the field device 104 and a second vibration sensing device 118 (e.g., an acceleration sensor, a motion sensor, a vibration sensor, etc.) affixed to the valve assembly 106. However, other installation locations may additionally or alternatively be utilized, such as the actuator 108, the valve 110, etc. Additional installation locations outside of the process control environment 102 may also be utilized. Although two vibration sensing devices are depicted in FIG. 1, one or more vibration sensing devices may be utilized. The terms acceleration field device, motion field device and/or vibration sensing device may be used interchangeably.

In the illustrated example, the vibration sensing devices 116,118 are coupled to the example structural condition monitor apparatus 100. Although depicted in FIG. 1 as coupled via one or more wires, the vibration sensing devices 116,118 may additionally or alternatively be connected via a wireless network. The example structural condition monitor apparatus 100 may be a process control system or a part of a process control system that includes a controller for data acquisition and processing. The example structural condition monitor apparatus 100 obtains acceleration information from the vibration sensing devices 116,118. In some examples, the vibration sensing devices 116,118 are analog transducers that output an analog electrical signal (e.g., a voltage amplitude) proportional to an amount of experienced acceleration in at least one orthogonal axis. In some instances, the vibration sensing devices 116,118 are digital transducers that output a digital electrical signal (e.g., a pulse-width modulated signal) proportional to the amount of acceleration experienced along at least one orthogonal axis. For example, the vibration sensing devices 116,118 may be a type of acceleration sensor (e.g., a capacitive accelerometer sensor, a hall effect accelerometer sensor, a piezoelectric resistive accelerometer sensor, etc.) that output a known voltage amplitude proportional to the amount of acceleration experienced along at least one orthogonal axis.

In the illustrated example of FIG. 1, the example structural condition monitor apparatus 100 obtains acceleration information from the vibration sensing devices 116,118 during operation to identify a difference in an operational acceleration response of the field device 104 in comparison to a baseline acceleration response of the field device 104. The difference in the operational acceleration response and the baseline acceleration response may be a difference in magnitude of obtained electrical signals (e.g., a difference in voltage), a difference trend (e.g., an increasing difference, a decreasing difference), etc. The difference in the acceleration response of the field device 104 may be related to a condition of the structure of the field device 104. The structural condition of the field device 104 may be a degradation in the structure such as, for example, a crack forming in the structure of the field device 104, a decoupling of a component attached to the structure of the field device 104, a decoupling of a component attached within the structure of the field device 104, etc. In some instances, the structural condition of the field device 104 may be a degradation of operating performance such as, for example, a corroded component failing in the actuator 108, a break in a pneumatic seal of the pneumatic tube connection 112, etc. Determining if the difference between the operational acceleration response and the baseline acceleration response of the field device 104 increases over time may indicate a degradation of the structural condition of the field device 104.

In the illustrated example of FIG. 1, the first vibration sensing device 116 is coupled to the field device 104 and the second vibration sensing device 118 is coupled to the valve assembly 106 to monitor a condition of the pneumatic tube connection 112 (e.g., a decoupling of the pneumatic tube connection 112). The first vibration sensing device 116 is installed in close proximity to a connection point between the field device 104 and the pneumatic tube connection 112. The first vibration sensing device 116 measures an acceleration response (e.g., an output acceleration response) of the connection point between the field device 104 and the pneumatic tube connection 112. The second vibration sensing device 118 is installed in close proximity to the source of vibration such as, for example, the valve 110 connected to the fluid process system 114. The second vibration sensing device 118 a measures an acceleration response (e.g., an input acceleration response) of the source of vibration. The example structural condition monitor apparatus 100 may calculate an operational acceleration response based on a ratio of the acceleration response as measured by the first vibration sensing device 116 and the acceleration response as measured by the second vibration sensing device 118. The example structural condition monitor apparatus 100 may determine a difference between the operational acceleration response and a baseline acceleration response (e.g., an expected acceleration response). The example structural condition monitor apparatus 100 may determine if the difference satisfies a threshold (e.g., the difference exceeds 1 volt, the difference exceeds 1 Hz, etc.). The example structural condition monitor apparatus 100 may generate an alert in response to the difference satisfying the threshold.

In the illustrated example, the example structural condition monitor apparatus 100 determines the difference between the operational acceleration response and the baseline acceleration response. In some examples, the example structural condition monitor apparatus 100 determines the baseline acceleration response by obtaining acceleration information from the vibration sensing devices 116,118 during a period of known good health for the field device 104. The example structural condition monitor apparatus 100 may use the known good health acceleration information for the field device 104 to generate at least one vibration model for the field device 104. The example structural condition monitor apparatus 100 may use the vibration model(s) for the field device 104 to determine the operational and baseline acceleration response of the field device 104. For example, the structural condition monitor apparatus 100 may enter obtained acceleration information from the vibration sensing devices 116,118 during operation (e.g., process control operating conditions) into a first vibration model to calculate the operational acceleration response. In another example, the structural condition monitor apparatus 100 may enter obtained acceleration information from the vibration sensing devices 116,118 during operation (e.g., process control operating conditions) into a second vibration model to calculate the baseline acceleration response.

In the illustrated example of FIG. 1, the example structural condition monitor apparatus 100 generates at least a first and second vibration model. The example structural condition monitor apparatus 100 may calculate a first acceleration response of the field device 104 by entering the obtained acceleration information during operation into the first vibration model. The first acceleration response of the field device 104 may be the operational acceleration response of the field device 104. The example structural condition monitor apparatus 100 may also calculate a second acceleration response for the field device 104 by entering a calculated parameter (e.g., a number of operating cycles, a time duration, etc.) into the second vibration model. The example structural condition monitor apparatus 100 may calculate the entered calculated parameter based on obtained acceleration information from the vibration sensing devices 116,118. The second acceleration response of the field device 104 may be a baseline and/or expected acceleration response. In some examples, the example structural condition monitor apparatus 100 compares the first and second acceleration responses of the field device 104 to determine if a difference between the first and second acceleration responses of the field device 104 satisfies a threshold (e.g., a difference exceeds 1 Hz). If the difference between the first and second acceleration responses of the field device 104 satisfies the threshold, then the example structural condition monitor apparatus 100 may identify a condition of the structure of the field device 104. In some instances, the example structural condition monitor apparatus 100 generates an alert (e.g., an alarm s sounded, an alert message is propagated in a process control network, etc.) in response to the difference satisfying the threshold.

Figure 2:
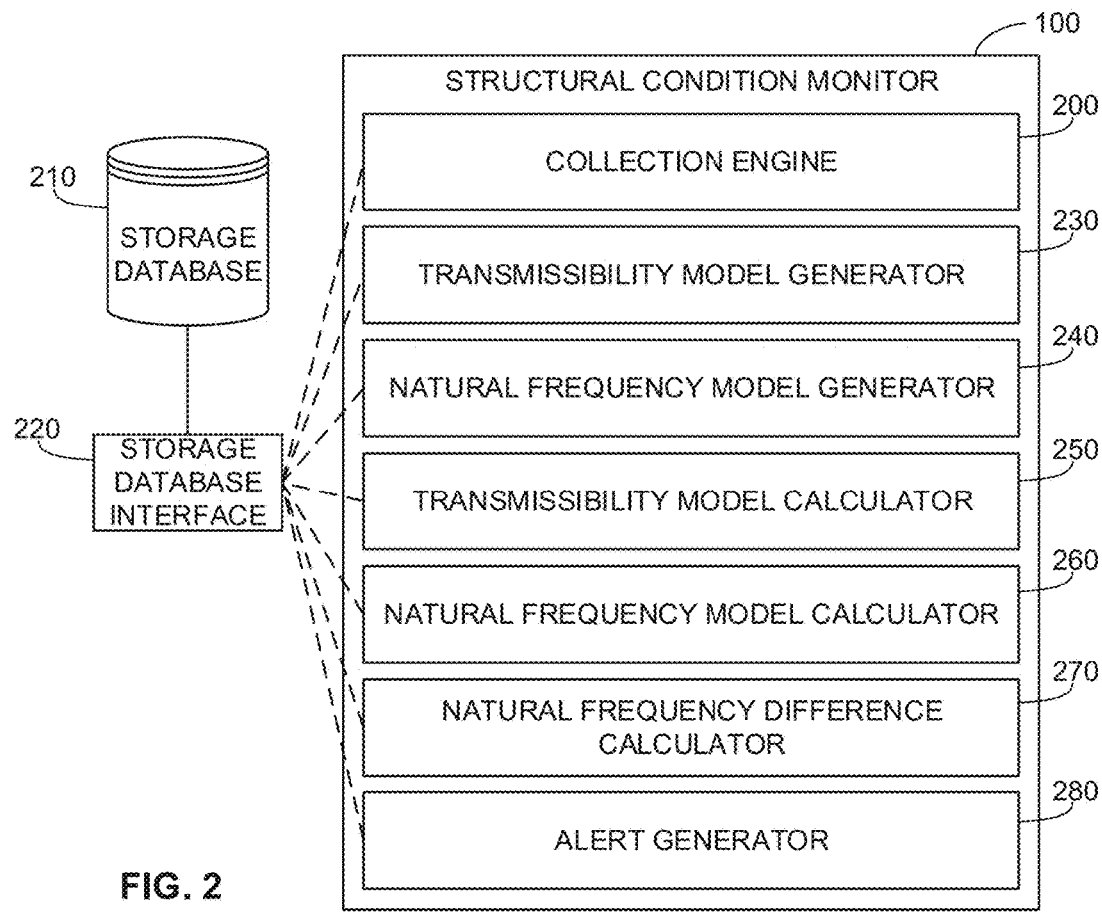
FIG. 2 is a block diagram of an example implementation of the example structural condition monitor of FIG. 1.

FIG. 2 is a block diagram of an example implementation of the structural condition monitor apparatus 100 of FIG. 1. The example structural condition monitor apparatus 100 determines if the difference between the operational acceleration response of the structure and the baseline acceleration response of the structure identifies the condition of the structure. For example, the structural condition monitor apparatus 100 may determine if the difference between the operational acceleration response of the field device 104 and the baseline acceleration response of the field device 104 identifies the structural condition of the field device 104. The example structural condition monitor apparatus 100 of FIG. 2 includes an example collection engine 200, an example storage database 210, an example storage database interface 220, an example transmissibility model generator 230, an example natural frequency model generator 240, an example transmissibility model calculator 250, an example natural frequency model calculator 260, an example natural frequency difference calculator 270, and an example alert generator 280. The example structural condition monitor apparatus 100 of FIG. 2 is communicatively coupled to the example storage database 210 via the example storage database interface 220.

In the illustrated example of FIG. 2, the example structural condition monitor apparatus 100 includes the example collection engine 200 to obtain acceleration information from at least one vibration sensing device (e.g., an acceleration sensor, a motion sensor, a vibration sensor, etc.), select acceleration information of interest and process the selected acceleration information of interest. In some examples, the example collection engine 200 obtains acceleration information from at least one vibration sensing device during a time period in which baseline acceleration information is obtained (e.g., during a post-manufacturing quality inspection, during a pre-operating commissioning procedure, etc.). For example, the collection engine 200 may operate as a baseline collection engine when obtaining baseline acceleration information to be used for generating one or more vibration models. In some instances, the example collection engine 200 obtains acceleration information from at least one vibration sensing device during a time period in which operational acceleration information is obtained. For example, the collection engine 200 may operate as an operational collection engine when obtaining acceleration information for the structure that is operating.

In the illustrated example of FIG. 2, the example collection engine 200 selects obtained acceleration information of interest to be used by one or more algorithms, processes, programs, etc. Selected obtained acceleration information may include, for example, an analog electrical signal, a digital electrical signal, etc. The example collection engine 200 processes the acceleration information by converting (e.g., converting using a conversion calculation, converting to different units of measure, etc.), scaling (e.g., scaling using a scaling factor), and/or translating (e.g., translating using a sensitivity curve) the electrical output from the vibration sensing device(s) to a measure of acceleration, motion and/or vibration that may be used by the example structural condition monitor apparatus 100. For example, the collection engine 200 may obtain a voltage amplitude from a piezoelectric accelerometer sensor affixed to the field device 104 experiencing an acceleration. The collection engine 200 may then translate the obtained voltage amplitude to a measure of the experienced acceleration. The example collection engine 200 may scale the obtained voltage amplitude to the measure of the experienced acceleration by using a scaling factor (e.g., a sensitivity scaling factor).

In the illustrated example of FIG. 2, the example structural condition monitor apparatus 100 may utilize the example storage database 210 to record data (e.g., obtained acceleration information, calculated parameter values etc.) via the example storage database interface 220. The example storage database 210 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., flash memory). The example storage database 210 may additionally or alternatively be implemented by one or more double data rate (DDR) memories, such as DDR, DDR2, DDR3, mobile DDR (mDDR), etc. The example storage database 210 may additionally or alternatively be implemented by one or more mass storage devices such as hard disk drive(s), compact disk drive(s) digital versatile disk drive(s), etc. While in the illustrated example the storage database 210 is illustrated as a single database, the storage database 210 may be implemented by any number and/or type(s) of databases.

In the illustrated example of HG. 2, the storage database interface 220 is a bus and/or network. For example, the storage database interface 220 may be an internal controller bus, a process control network, etc. In some examples, the storage database interface 220 is a network with the capability of being communicatively coupled to the Internet. However, the example storage database interface 220 may be implemented using any suitable wired and/or wireless network(s) including, for example, one or more data buses, one or more Local Area Networks (LANs), one or more wireless LANs, one or more cellular networks, one or more private networks, one or more public networks, etc. The example storage database interface 220 enables the example structural condition monitor apparatus 100 to be in communication with the storage database 210. As used herein, the phrase "in communication," including variances thereof, encompasses direct communication and/or indirect communication through one or more intermediary components and does not require direct physical (e.g., wired) communication and/or constant communication, but rather includes selective communication at periodic or aperiodic intervals, as well as one-time events.

In the illustrated example of FIG. 2, the example structural condition monitor apparatus 100 includes the example transmissibility model generator 230 to generate a transmissibility model for the structure. In some examples, the example transmissibility model generator 230 is configured to generate the transmissibility model for the structure by performing a curve fit for calculated transmissibility information. The example transmissibility model generator 230 uses acceleration information obtained by the example collection engine 200 from two or more vibration sensing devices to generate the transmissibility model. The transmissibility model for the structure characterizes a ratio of an output acceleration response measured at a first location and an input acceleration response measured at a second location as a function of frequency. In some examples, the output acceleration response measured at the first location is the acceleration response of the structure. In some instances, the input acceleration response measured at the second location is the acceleration response measured at a source of vibration or measured in closer proximity to the source of the vibration. For example, the transmissibility model generator 230 may generate the transmissibility model characterizing a ratio of the field device 104 acceleration response and the valve assembly 106 acceleration response as a function of frequency. The example structural condition monitor apparatus 100 may use the transmissibility model generated by the example transmissibility model generator 230 to calculate a natural frequency of the field device 104.

In the illustrated example of FIG. 2, the example transmissibility model generator 230 uses the obtained acceleration information to calculate the transmissibility of the structure. The example transmissibility model generator 230 calculates the transmissibility by calculating a ratio of the acceleration response of the structure measured at a first location and an acceleration response measured at a second location obtained by a first and second vibration sensing device. For example, the transmissibility model generator 230 may calculate a ratio of the acceleration response of the field device 104 measured by the first vibration sensing device 116 and the acceleration response of the valve assembly 106 measured by the second vibration sensing device 118. The example transmissibility model generator 230 may identify a frequency at which resonance occurs by determining a frequency at which a maximum transmissibility occurs. In some instances, the example transmissibility model generator 230 calculates and optimizes transmissibility parameters for the generation of the transmissibility model used to characterize the structure. The example transmissibility model generator 230 may also identify and eliminate outliers in the obtained acceleration information to further optimize the generated transmissibility model used to characterize the structure. For example, the structural condition monitor apparatus 100 may eliminate outliers in the acceleration information used to optimize the generated transmissibility model characterizing the field device 104.

In the illustrated example of FIG. 2, the example structural condition monitor apparatus 100 includes the example natural frequency model generator 240 to generate a natural frequency model for the structure. In some examples, the example natural frequency model generator 240 is configured to generate the natural frequency model for the structure by performing a curve fit for calculated natural frequency information. The natural frequency model for the structure characterizes a natural frequency of the structure as a function of time (e.g., a time interval). The example natural frequency model generator 240 uses acceleration information obtained by the example collection engine 200 from one or more vibration sensing devices to generate the natural frequency model. The example structural condition monitor apparatus 100 may use the natural frequency model generated by the example natural frequency model generator 240 to calculate a natural frequency of the field device 104. The natural frequency of the field device 104 calculated with the natural frequency model generated by the natural frequency model generator 240 may be in addition to the natural frequency of the field device 104 calculated with the transmissibility model generated by the example transmissibility model generator 230.

In the illustrated example of FIG. 2, the example natural frequency model generator 240 calculates an average natural frequency for a number of acceleration responses obtained from one or more acceleration sensors during a period of known good health for the field device 104. In some examples, the example natural frequency model generator 240 calculates a natural frequency for each acceleration response of interest. For each acceleration response of interest, the example natural frequency model generator 240 calculates a difference between the calculated natural frequency for the acceleration response of interest and the calculated average natural frequency for the number of acceleration responses. In some instances, the example natural frequency model generator 240 calculates an average for a number of the calculated differences, or herein referred to as the calculated average natural frequency difference. For an acceleration response of interest, the example natural frequency model generator 240 may generate a linear fit model including at least a slope and y-intercept. In some examples, the example natural frequency model generator 240 calculates the slope of the linear fit by calculating a ratio of the calculated average natural frequency difference and the number of acceleration responses. In some instances, the example natural frequency model generator 240 identifies the y-intercept of the linear fit as the calculated average natural frequency for the number of acceleration responses.

In the illustrated example of FIG. 2, the example structural condition monitor apparatus 100 includes the example transmissibility model calculator 250 to calculate the natural frequency of a structure by entering the obtained acceleration information by the example collection engine 200 into the transmissibility model generated by the example transmissibility model generator 230. In some examples, the example transmissibility model calculator 250 calculates the transmissibility of the structure. The example transmissibility model calculator 250 may then enter the calculated transmissibility into the generated transmissibility model to calculate the natural frequency of the structure. For example, the transmissibility model calculator 250 may calculate the transmissibility of the field device 104 during a time period in which the field device 104 is experiencing vibration. The example transmissibility model calculator 250 may enter the obtained acceleration information from the vibration sensing devices 116,118 into the generated transmissibility model. The example transmissibility model calculator 250 may calculate the natural frequency for the field device 104 in response to calculating the transmissibility of the field device 104.

In the illustrated example of FIG. 2, the example structural condition monitor apparatus 100 includes the example natural frequency model calculator 260 to calculate the natural frequency of the structure by entering the obtained acceleration information by the example collection engine 200 into the natural frequency model generated by the example natural frequency model generator 240. In some examples, the example natural frequency model calculator 260 calculates a number of cycles (e.g., a number of operating cycles, a number of vibration cycles, etc. experienced by the structure. The number of vibration cycles may be calculated by multiplying the calculated average natural frequency calculated by the example natural frequency model generator 240 and the time between data and/or information samples obtained by the collection engine 200. The example natural frequency model calculator 260 may enter the calculated number of cycles into the generated natural frequency model to calculate the natural frequency of the structure. For example, the natural frequency model calculator 260 may calculate the natural frequency of the field device 104 during a time period in which the field device 104 is experiencing vibration. The example natural frequency model calculator 260 may enter the obtained acceleration information (e.g., the number of calculated vibration cycles) from the vibration sensing devices 116,118 into the generated natural frequency model. The example natural frequency model calculator 260 may calculate the natural frequency for the field device 104 in response to calculating the number of vibration cycles experienced by the field device 104.

In the illustrated example of FIG. 2, the example structural condition monitor apparatus 100 includes the example natural frequency difference calculator 270 to calculate a difference between a first natural frequency of a structure calculated by the transmissibility model generated by the transmissibility model generator 230 and a second natural frequency of the structure calculated by the natural frequency model calculated by the natural frequency model generator 240. In some examples, the first natural frequency of the structure calculated by the transmissibility model is the operational natural frequency. In some examples, the second natural frequency of the structure calculated by the natural frequency model is the baseline and/or expected natural frequency. In some instances, the difference between the first and second calculated natural frequencies increases as the structure experiences increased periods of vibration. For example, the difference between the first calculated natural frequency (e.g., the operational natural frequency) and the second calculated natural frequency (e.g., the baseline natural frequency) of the field device 104 may increase over time as the field device 104 experiences accelerated wear due to increased exposure to vibration.

In the illustrated example of FIG. 2, the example structural condition monitor apparatus 100 includes the example alert generator 280 to evaluate the difference (e.g., the magnitude of the difference) between the first and second calculated natural frequencies of the structure and to generate an alert if the difference satisfies a threshold. In some examples, the example alert generator 280 employs a predefined threshold that may be dependent on user input. In some instances, the example alert generator 280 utilizes a calculated threshold that may be dependent on at least one factor such as, for example, a number of standard deviations within the difference between the first and second calculated natural frequencies during the period of known good health. If the example alert generator 280 determines that the difference between the first and second calculated natural frequencies satisfies the threshold (e.g., the difference exceeds 1 Hz), then the alert generator 280 may identify the condition of the structure. For example, the alert generator 280 may identify the condition of the structure to be a degradation of the structure (e.g., an initial crack formation in the structure, a propagation of a crack formation in the structure, etc.), a deterioration in the performance of the structure (e.g., a propagation of a crack in a seal), a failing of the structure (e.g., the actuator 108 cannot move, the valve 110 can no longer hold pressure etc.), etc. In response to identifying the condition of the structure, the example alert generator 280 may generate an alert such as, for example, sounding an alarm, propagating an alert message throughout a process control network, generating a failure log and/or report, etc.

While an example manner of implementing the example structural condition monitor apparatus 100 is illustrated in FIG. 2, one or more of the elements, processes and/or devices illustrated in FIG. 2 may be combined, divided, re-arranged, omitted, eliminated and/or implemented in any other way. Further, the example collection engine 200, the example storage database 210, the example storage database interface 220, the example transmissibility model generator 230, the example natural frequency model generator 240, the example transmissibility model calculator 250, the example natural frequency model calculator 260, the example natural frequency difference calculator 270, the example alert generator 280, and/or, more generally, the example structural condition monitor apparatus 100 of FIG. 2 may be implemented by hardware, software, firmware and/or any combination of hardware, software and/or firmware. Thus, for example, any of the example collection engine 200, the example storage database 210, the example storage database interface 220, the example transmissibility model generator 230, the example natural frequency model generator 240, the example transmissibility model calculator 250, the example natural frequency model calculator 260, the example natural frequency difference calculator 270, the example alert generator 280 and/or, more generally, the example structural condition monitor apparatus 100 of FIG. 2 may be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example collection engine 200, the example storage database 210, the example storage database interface 220, the example transmissibility model generator 230, the example natural frequency model generator 240, the example transmissibility model calculator 250, the example natural frequency model calculator 260, the example natural frequency difference calculator 270, the example alert generator 280 and/or, more generally, the example structural condition monitor apparatus 100 of FIG. 2 is/are hereby expressly defined to include a tangible computer-readable storage device or storage disk such as a memory, a digital versatile disk (DVD), a. compact disk (CD), a Blu-ray disk, etc. storing the software and/or firmware. Further still, the example structural condition monitor apparatus 100 of FIG. 2 may include one or more elements, processes and/or devices in addition to, or instead of, those illustrated in FIG. 2, and/or may include more than one of any or all of the illustrated elements, processes and devices.

Flowcharts representative of example methods for implementing the example structural condition monitor apparatus 100 of FIG. 2 are shown in FIGS. 3-13. In these examples, the methods may be implemented using machine readable instructions that comprise a program for execution by a processor such as the processor 1412 shown in the example processor platform 1400 discussed below in connection with FIG. 14. The program may be embodied in software stored on a tangible computer-readable storage medium such as a CD-ROM, a floppy disk, a hard drive, a digital versatile disk (DVD), a Blu-ray disk, or a memory associated with the processor 1412, but the entire program and/or parts thereof may alternatively be executed by a device other than the processor 1412 and/or embodied in firmware or dedicated hardware. Further, although the example program is described with reference to the flowcharts illustrated in FIGS. 3-13, many other methods of implementing the example structural condition monitor apparatus 100 may alternatively be used. For example, the order of execution of the blocks may be changed, and/or some of the blocks described may be changed, eliminated, or combined.

As mentioned above, the example methods of FIGS. 3-13 may be implemented using coded instructions (e.g., computer and/or machine readable instructions) stored on a tangible computer-readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer-readable storage medium is expressly defined to include any type of computer-readable storage device and/or storage disk and to exclude propagating signals and to exclude transmission media. As used herein, "tangible computer-readable storage medium" and "tangible machine-readable storage medium" are used interchangeably. Additionally or alternatively, the example methods of FIGS. 3-13 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer-readable medium is expressly defined to include any type of computer-readable storage device and/or storage disk and to exclude propagating signals and to exclude transmission media. As used herein, when the phrase "at least" is used as the transition term in a preamble of a claim, it is open-ended in the same manner as the term "comprising" is open ended. Comprising and all other variants of "comprise" are expressly defined to be open-ended terms. Including and all other variants of "include" are also defined to be open-ended terms. In contrast, the term consisting and/or other forms of consist are defined to be close-ended terms.

Figure 3:
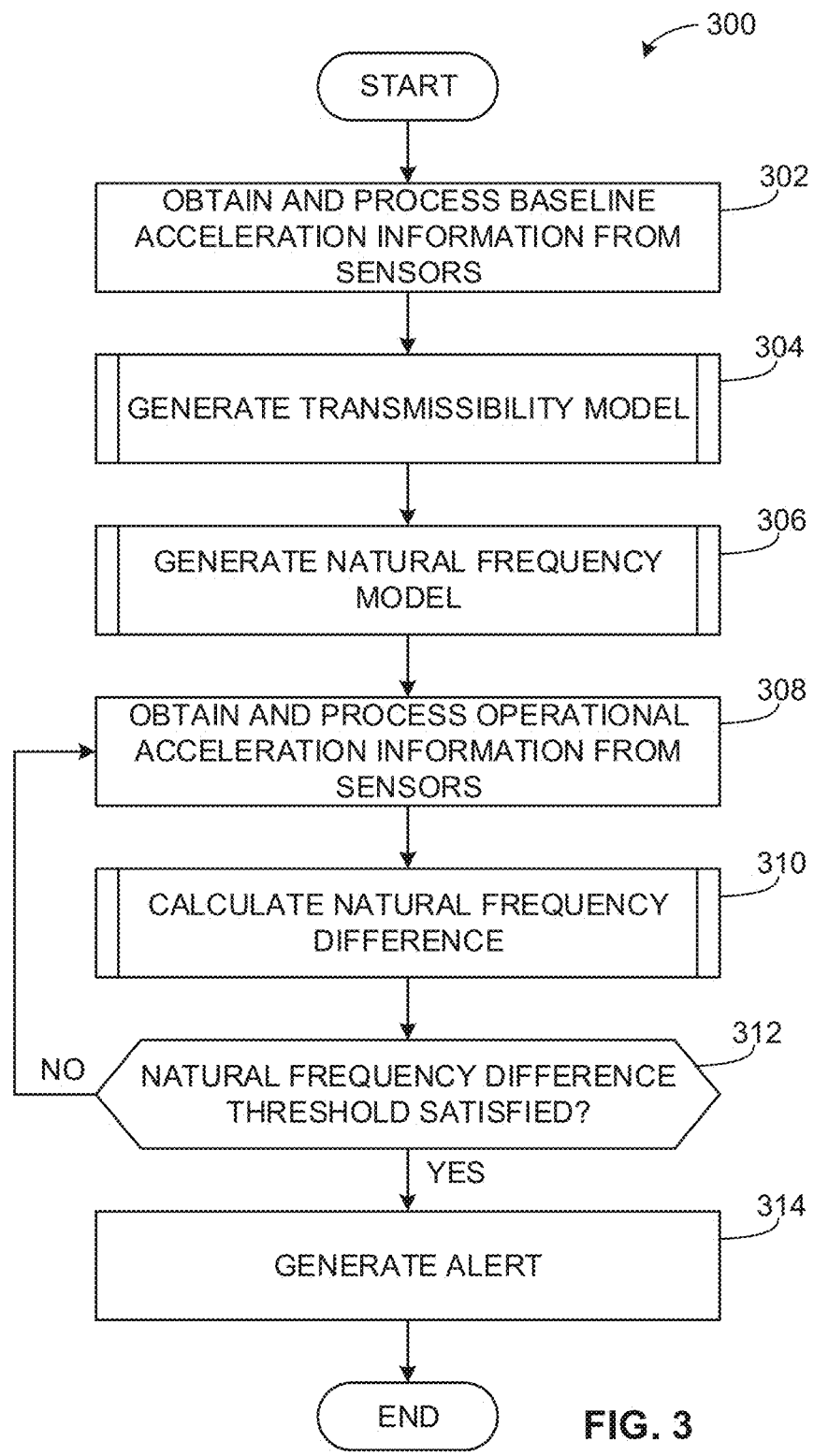
FIGS. 3-13 are flowcharts representative of example methods that may be performed using the example structural condition monitor of FIG. 1 to monitor a condition of a structure.

FIG. 3 is a flowchart representative of an example method 300 that may be performed by the example structural condition monitor apparatus 100 of FIG. 2 to identify a condition of a structure. For example, the structure may be the field device 104 and the condition of the structure may be the condition of the pneumatic tube connection 112 (e.g., the pneumatic tube connection 112 is decoupling). The example method 300 begins at block 302 when the example structural condition monitor apparatus 100 obtains and processes acceleration information from the vibration sensing devices 116,118 in the process control environment 102. In some examples the example structural condition monitor apparatus 100 may process the obtained acceleration information by converting, scaling, and/or translating the electrical outputs of the vibration sensing devices 1.16,118 into a measure of acceleration, motion, and/or vibration experienced by the field device 104.

At block 304, the example structural condition monitor apparatus 100 generates the transmissibility model for the structure. For example, the structural condition monitor apparatus 100 may calculate the transmissibility for the field device 104 to determine the natural frequency for the field device 104. The example structural condition monitor apparatus 100 may use the natural frequency for the field device 104 to further calculate additional transmissibility parameters and optimize the additional transmissibility parameters to generate the transmissibility model for the field device 104. At block 306, the example structural condition monitor apparatus 100 generates the natural frequency model. For example, the structural condition monitor apparatus 100 may calculate an average natural frequency for the field device 104 during a period of known good health. The example structural condition monitor apparatus 100 may also calculate a slope and a y-intercept of a linear fit to generate the natural frequency model.

At block 308, the example structural condition monitor apparatus 100 obtains and processes acceleration information from one or more vibration sensing devices. For example, the structural condition monitor apparatus 100 may obtain and process acceleration information from the vibration sensing devices 116,118. At block 310, the example structural condition monitor apparatus 100 calculates a difference between a first natural frequency calculated by the transmissibility model and a second natural frequency calculated by the natural frequency model. For example, the structural condition monitor apparatus 100 may calculate the difference between the first natural frequency calculated by the transmissibility model used to characterize the field device 104 and the second natural frequency calculated by the natural frequency model used to characterize the field device 104.

At block 312, the example structural condition monitor apparatus 100 determines if the difference between the first and second calculated natural frequencies satisfies a threshold (e.g., the difference is greater than or equal to a threshold). For example, the structural condition monitor apparatus 100 may determine if the difference between the first and second calculated natural frequencies is greater than or equal to 1 Hz. If, at block 312, the example structural condition monitor apparatus 100 determines that the difference between the first and second calculated natural frequencies does not satisfy the threshold, then control returns to block 308 to obtain and process additional acceleration information from the vibration sensing devices during operation. If, at block 312, the example structural condition monitor apparatus 100 determines that the difference between the first and second calculated natural frequencies does satisfy the threshold, then, at block 314, the structural condition monitor apparatus 100 generates an alert identifying the condition of the structure. For example, the alert may be a text-based alarm in a process control software indicating that the pneumatic tube connection 112 is decoupling from the field device 104.

Figure 4:
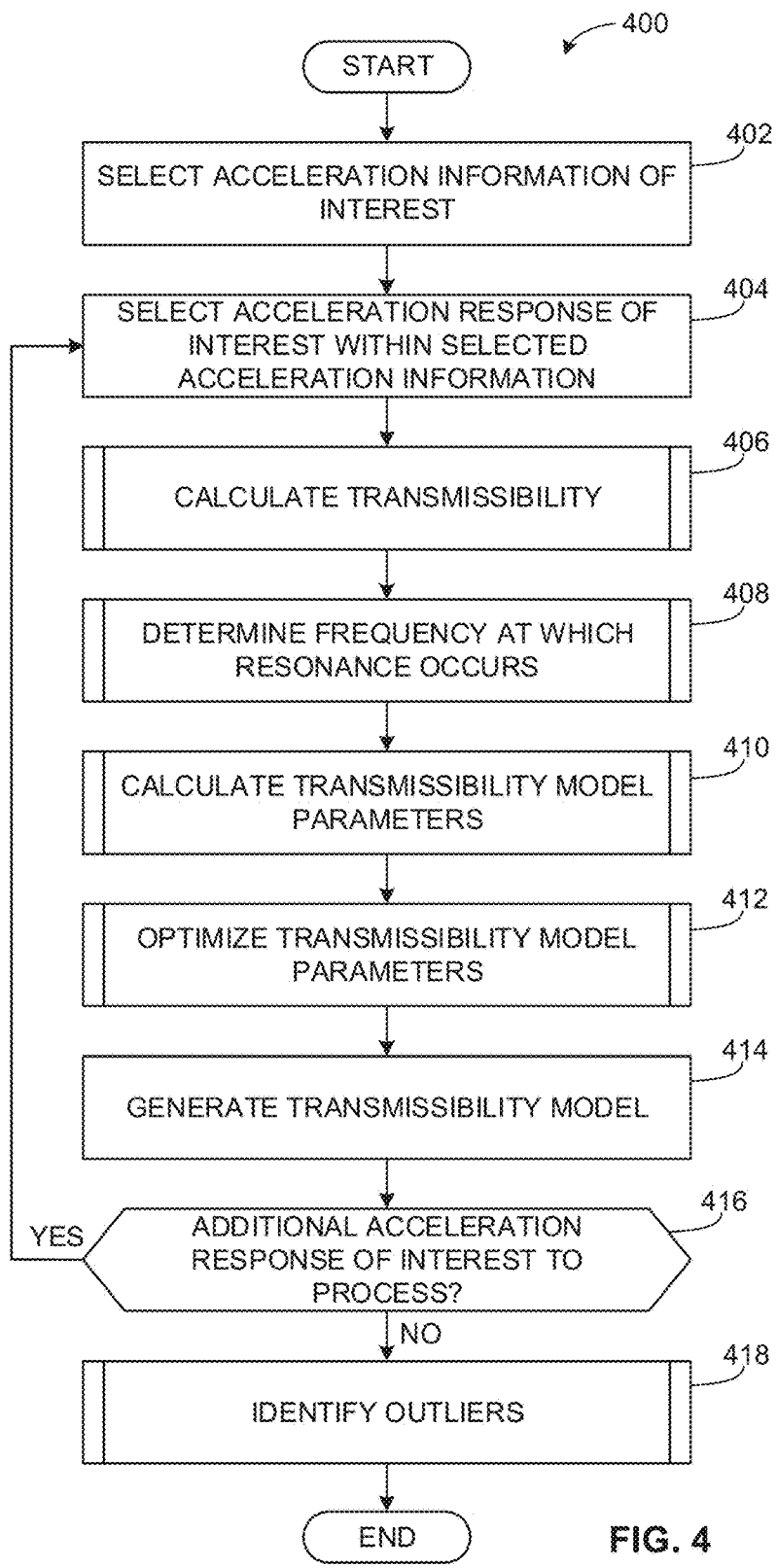

Additional detail in connection with generating the transmissibility model (FIG. 3 block 304) is shown in FIG. 4. FIG. 4 is a flowchart representative of an example method 400 that may be performed by the example structural condition monitor apparatus 100 of FIG. 2 to generate the transmissibility model characterizing the transmissibility of a structure. The example method 400 begins at block 402 when the example structural condition monitor apparatus 100 selects acceleration information of interest to process. In some examples, the example structural condition monitor apparatus 100 obtains the selected acceleration information of interest from one or more vibration sensing devices monitoring the structure in known good health. For example, the example structural condition monitor apparatus 100 may obtain the selected acceleration information of interest from the vibration sensing devices 116, 118 monitoring the field device 104 during a time period in which the field device 104 is known to be in good health (e.g., no defects, no degradation of performance, no impending failure conditions, etc.). A time period in which the field device 104 is known to be in good health may be the time period following the manufacturing of the field device 104, the time period following the first commissioning of the field device 104 for operation, etc.

At block 404, the example structural condition monitor apparatus 100 selects an acceleration response within the selected acceleration information of interest to process. In some examples, the selected acceleration response may be a data set of acceleration information collected during a defined time interval or during a time period in which an event occurs. For example, the selected acceleration response may be the acceleration data collected during a periodic time interval (e.g., every 100 milliseconds) and/or the acceleration data collected during a time period in which an event occurs such as, for example, the actuator 108 moving from an open position to a closed position, the valve 110 moving from an open position to a closed position, etc.

At block 406, the example structural condition monitor apparatus 100 calculates the transmissibility of the field device 104. In some examples, the transmissibility of the field device 104 may have real and/or imaginary components. For example, the structural condition monitor apparatus 100 calculates the real component of the ratio of the acceleration information of the field device 104 obtained by the vibration sensing device 116 and the acceleration information of the valve assembly 106 obtained by the vibration sensing device 118. At block 408, the example structural condition monitor apparatus 100 determines a frequency at which resonance occurs. For example, the structural condition monitor apparatus 100 may identify resonance at the maximum transmissibility (real) value.

At block 410, the example structural condition monitor apparatus 100 calculates one or more transmissibility model parameters such as, for example, an amplitude, a bandwidth, a damping ratio, one or more half power frequencies, a natural frequency, a quality factor, a vertical shift, etc. At block 412, the example structural condition monitor apparatus 100 optimizes at least one of the transmissibility model parameters calculated at block 410 using a recursive optimization method. For example, the structural condition monitor apparatus 100 may optimize the transmissibility model parameters by using a sum of squared errors (SSE) optimization method. The SSE optimization method may first estimate the transmissibility model parameters and then modify the transmissibility model parameters until the SSE between the generated transmissibility model and the measured transmissibility is minimized, where the measured transmissibility is based on the obtained operational acceleration information. For example, the structural condition monitor apparatus 100 may use the observed acceleration information within the selected acceleration response of interest to calculate initial set points for the one or more transmissibility model parameters as described above. The structural condition monitor apparatus 100 may use the SSE optimization method to identify the values of the transmissibility model parameters that minimizes the summed squared error.

At block 414, the example structural condition monitor apparatus 100 generates the transmissibility model using the optimized parameters calculated at block 412. In some examples, the transmissibility model is generated to be in accordance with example Equation (1) below.

$$T = A\left(\frac{\left(1 + i\delta\left(\frac{f}{f_n}\right)\right)}{\left(1 - \left(\frac{f}{f_n}\right)^2 + \left(i2\delta\left(\frac{f}{f_n}\right)\right)\right)}\right) \quad \text{Equation (1)}$$

In the illustrated example of Equation (1), the variable "T" represents the transmissibility. The variable "A" represents the amplitude, the variable "δ" represents the damping ratio, the term "i" represents the imaginary component and/or portion, and the variables "f" and "$f_n$" represent the frequency and natural frequency, respectively. In the illustrated example of Equation (1), the transmissibility, at a specified frequency, is calculated using the amplitude, the damping ratio, and the natural frequency of a selected acceleration response of interest within selected acceleration information of interest. In some examples, the structural condition monitor apparatus uses the optimized parameters calculated at block 412 for the amplitude variable, the damping ratio variable, and the natural frequency variable of Equation (1). In some instances, the structural condition monitor apparatus 100 uses the calculated transmissibility calculated at block 406 for the transmissibility variable of Equation (1). In some examples, one or more half power frequencies and the vertical shift is added to Equation (1) to yield a magnitude of one or more half power points. In some instances, the half power points are the frequencies at which the power of an electrical signal has dropped to a half of its mid-band value.

In the illustrated example of FIG. 4, at block 416, the example structural condition monitor apparatus 100 determines if there is an additional acceleration response of interest to process. If, at block 416, the example structural condition monitor apparatus 100 determines there is at least one additional acceleration response of interest to process, control proceeds to block 404 to select an additional acceleration response of interest to process within the selected acceleration information of interest. If, at block 416, the example structural condition monitor apparatus 100 determines that there is no additional acceleration response of interest to process, then, at block 418, the structural condition monitor apparatus 100 analyzes (e.g., iteratively analyzes) the generated transmissibility models for the selected acceleration information of interest to identify and eliminate outliers.

Figure 5:
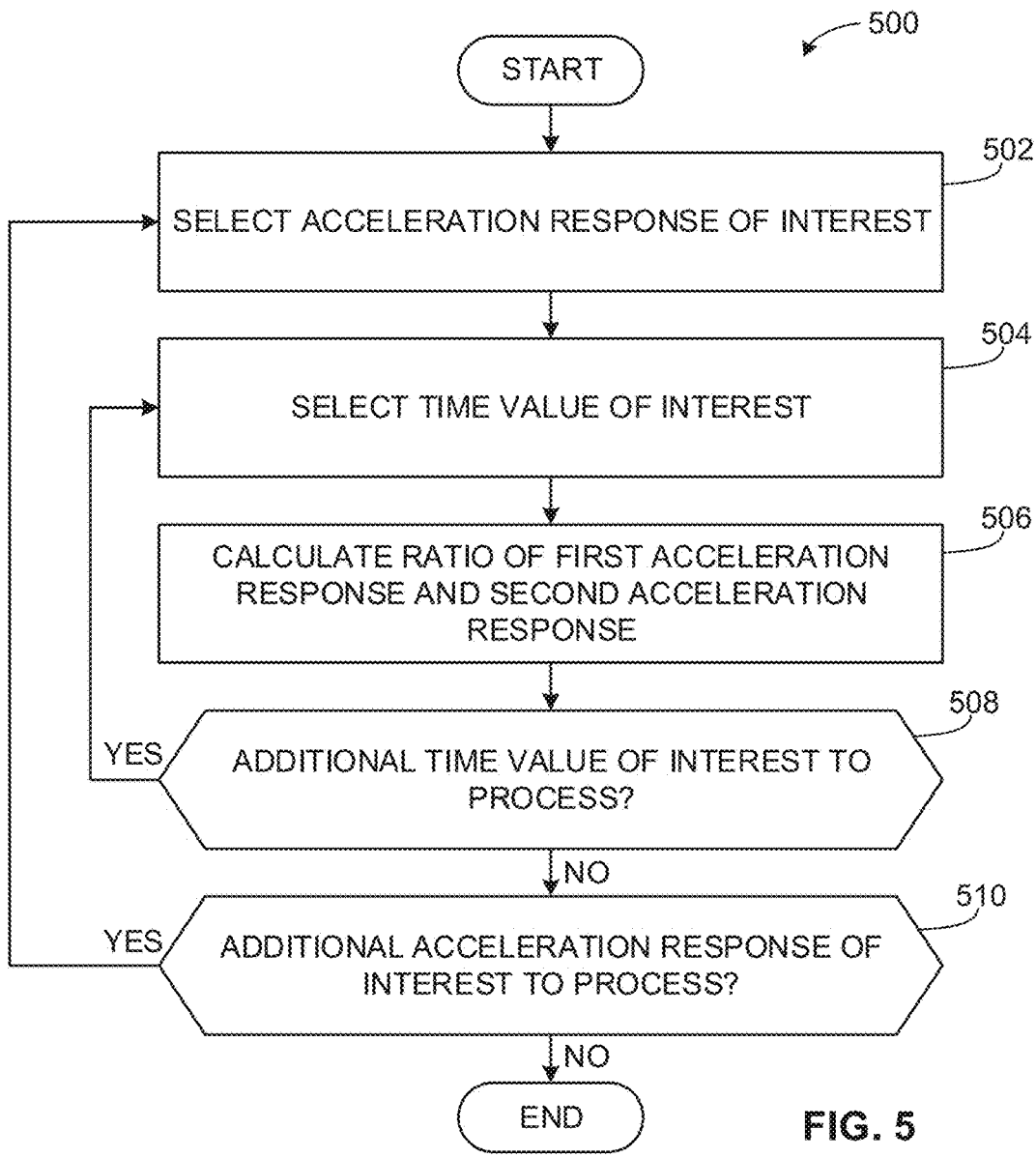

Additional detail in connection with calculating the transmissibility of the structure (FIG. 4 block 406) is shown in FIG. 5. FIG. 5 is a flowchart representative of an example method 500 that may be performed by the example structural condition monitor apparatus 100 of FIG. 2 to calculate the transmissibility of structure. For example, the structure may be the field device 104. The example method 500 begins at block 502 when the example structural condition monitor apparatus 100 selects acceleration information of interest to process. The selected acceleration information of interest to process may include, for example, acceleration information obtained from at least one vibration sensing device. For example, the selected acceleration information of interest to process may include the acceleration information obtained from the vibration sensing devices 116,118. At block 504, the example structural condition monitor apparatus 100 selects a time value of interest to analyze the selected acceleration information from the vibration sensing devices 116,118. For example, the structural condition monitor apparatus 100 may select a starting time, a time period, etc. A time value may be selected to synchronize the acceleration information obtained from the vibration sensing devices 116,118.

At block 506, the example structural condition monitor apparatus 100 calculates a ratio of the first acceleration response obtained from the first vibration sensing device 116 and the second acceleration response obtained from the second vibration sensing device 118. In some examples, a real and imaginary portion of the ratio may be calculated. One or both portions of the ratio may be utilized by the example structural condition monitor apparatus 100 for processing. For example, the structural condition monitor apparatus 100 may calculate a ratio of the real portion of the first acceleration response obtained from the first vibration sensing device 116 and the real portion of the second acceleration response obtained from the second vibration sensing device 118. At block 508, the example structural condition monitor apparatus 100 determines if there is an additional ti value of interest within the selected acceleration response of interest to process. If, at block 508, the example structural condition monitor apparatus 100 determines there is an additional time value of interest to process, control proceeds to block 504 to select an additional time value of interest. If, at block 508, the example structural condition monitor apparatus 100 determines there is not an additional time value of interest to process, then, at block 510, the structural condition monitor apparatus 100 determines if there is an additional acceleration response of interest. If, at block 510, the example structural condition monitor apparatus 100 determines there is an additional acceleration response of interest to process, control proceeds to block 502 to select an additional acceleration response of interest, otherwise the example method 500 concludes.

Figure 6:
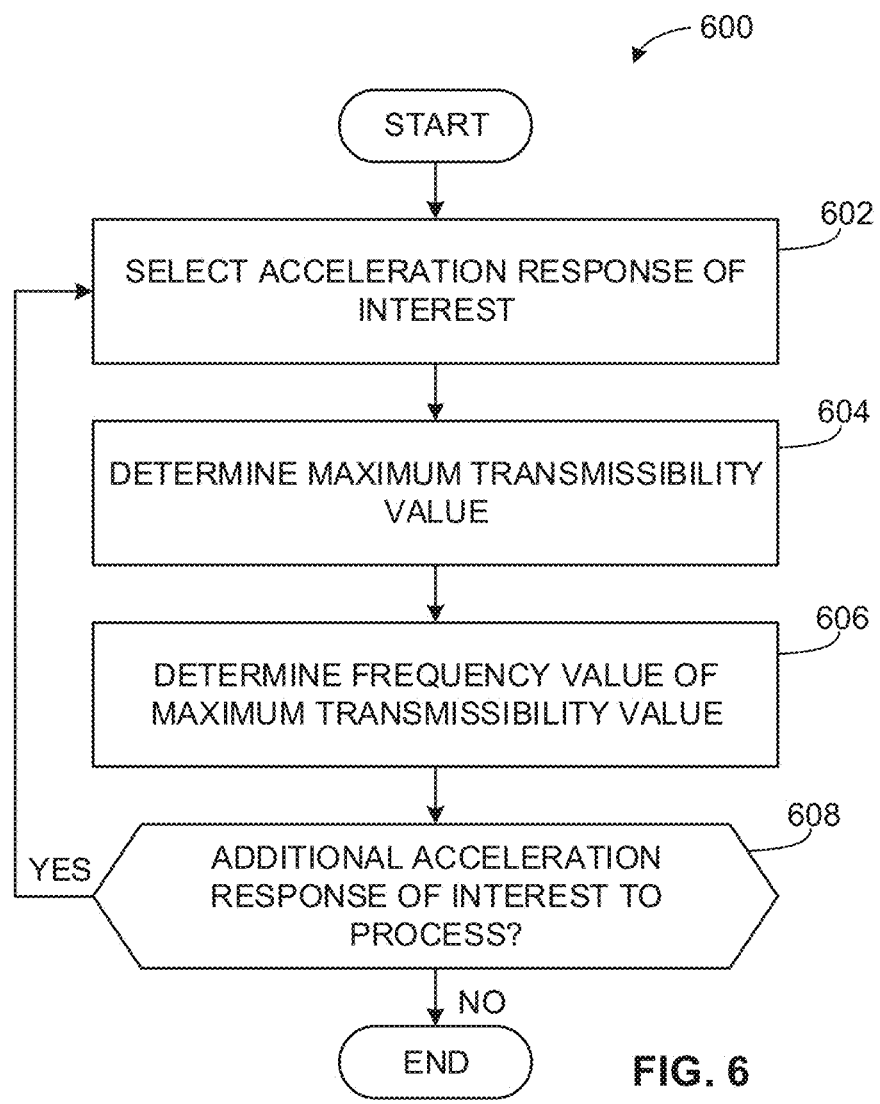

Additional detail in connection with determining the frequency at which resonance occurs (FIG. 4 block 408) is shown in FIG. 6. FIG. 6 is a flowchart representative of an example method 600 that may be performed by the example structural condition monitor apparatus 100 of FIG. 2 to determine the frequency at which resonance occurs for the structure. The example method 600 begins at block 602 when the example structural condition monitor apparatus 100 selects an acceleration response of interest to process. At block 604, the example structural condition monitor apparatus 100 determines the maximum transmissibility value for the selected acceleration response of interest. At block 606, the example structural condition monitor apparatus 100 determines the frequency at which the maximum transmissibility value occurs. In some examples, the example structural condition monitor apparatus 100 identifies the frequency at which the maximum transmissibility value occurs as the frequency at which resonance occurs. At block 608, the example structural condition monitor apparatus 100 determines if there is an additional acceleration response of interest to process. If, at block 608, the example structural condition monitor apparatus 100 determines there is an additional acceleration response of interest to process, control proceeds to block 602 to select an additional acceleration response of interest, otherwise the example method 600 concludes.

Figure 7:
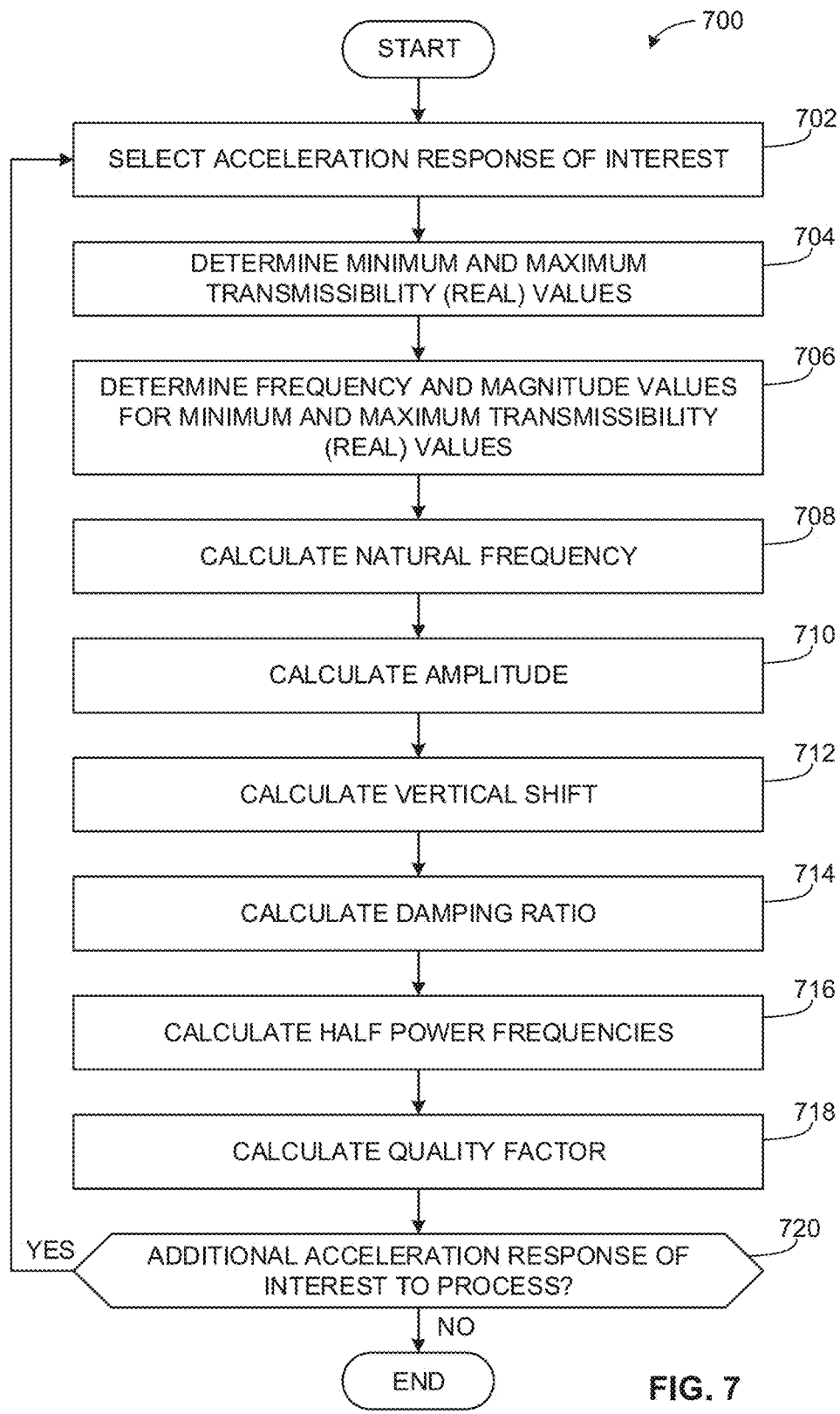

Additional detail in connection with calculating the transmissibility model parameters for the transmissibility model (FIG. 4 block 410) is shown in FIG. 7. FIG. 7 is a flowchart representative of an example method 700 that may be performed by the example structural condition monitor apparatus 100 of FIG. 2 to calculate the transmissibility model parameters for the transmissibility model used to characterize the field device 104. The example method 700 begins at block 702 when the example structural condition monitor apparatus 100 selects an acceleration response of interest. At block 704, the example structural condition monitor apparatus 100 determines the real portion of the minimum and maximum transmissibility values. At block 706, the example structural condition monitor apparatus 100 determines the frequency at which the real portion of the minimum and maximum transmissibility values occur and the magnitude of the real portion of the minimum and maximum transmissibility values.

At block 708, the example structural condition monitor apparatus 100 calculates the natural frequency for the transmissibility model. For example, the structural condition monitor apparatus 100 may use example Equation (2) below to calculate the natural frequency for the transmissibility model.

$$f_n = \frac{1}{2}(f_{Tmax} + f_{Tmin}) \quad \text{Equation (2)}$$

In the illustrated example of Equation (2) above, the variable "$f_n$" represents the natural frequency. The variable "$f_{T_{max}}$" represents the frequency at which the maximum transmissibility occurs and the variable "$f_{T_{min}}$" represents the frequency at which the minimum transmissibility occurs. At block 710, the example structural condition monitor apparatus 100 calculates the amplitude for the transmissibility model. For example, the structural condition monitor apparatus 100 may use example Equation (3) below to calculate the amplitude for the transmissibility model.

$$A = \frac{1}{2}|(T_{max} + T_{min})| \quad \text{Equation (3)}$$

In the illustrated example of Equation (3) above, the variable "A" represents the amplitude. The variable "$T_{max}$" represents the real portion of the maximum transmissibility value and the variable "$T_{min}$" represents the real portion of the minimum transmissibility value. The amplitude may be calculated in accordance with Equation (3) above as half of the absolute value of the sum of the real portions of the maximum and minimum transmissibility values. At block 712, the example structural condition monitor apparatus 100 calculates the vertical shift of the transmissibility model. For example, the structural condition monitor apparatus 100 may calculate the vertical shift by determining the minimum distance between a transmissibility curve and the transmissibility curve's horizontal axis.

At block 714, the example structural condition monitor apparatus 100 calculates the damping ratio for the transmissibility model. For example, the structural condition monitor apparatus 100 may use example Equation (4) below to calculate the damping ratio for the transmissibility model.

$$\delta = \left(\frac{1}{2*\left(\frac{f}{f_n}\right)}\right)\sqrt{\frac{A\left(1-\left(\frac{f}{f_n}\right)^2\right)}{T} + 1 + \left(\left(\frac{f}{f_n}\right)^2 * \left(\left(\frac{f}{f_n}\right)^2 - 2\right)\right)}$$

Equation (4)

In the illustrated example of Equation (4) above, the variable "δ" represents the damping ratio. The variable "f" represents the frequency, the variable "$f_n$" represents the natural frequency, the variable "A" represents the amplitude and the variable "T" represents the transmissibility. In some examples the real portion of the transmissibility is used for Equation (4) above. In some instances, the damping ratio used for the transmissibility model is calculated by calculating an average of the real part of the damping ratio values, calculated over the entire acceleration response of interest.

At block 716, the example structural condition monitor apparatus 100 calculates the half power frequencies for the transmissibility model. For example, the structural condition monitor apparatus 100 may use example Equation (5) below to calculate the half power frequencies for the transmissibility model.

$$f_{1,2} = f_n\sqrt{(1-(2\delta^2)) \pm (2\delta\sqrt{\delta^2+1})}$$

Equation (5)

In the illustrated example of Equation (5), the variable "$f_{1,2}$" represents a half power frequency. The variable "$f_n$" represents the natural frequency and the variable "δ" represents the damping ratio. At block 718, the example structural condition monitor apparatus 100 calculates the quality factor. In some examples, the quality factor is defined as the resonance peak and is calculated by calculating the midpoint between the half power frequencies as calculated by using example Equation (5) above. At block 720, the example structural condition monitor apparatus 100 determines if there is an additional acceleration response of interest to process. If, at block 720, the example structural condition monitor apparatus 100 determines that there is an additional acceleration response of interest to process, control proceeds to block 702 to select an additional acceleration response of interest, otherwise the example method 700 concludes.

Figure 8:
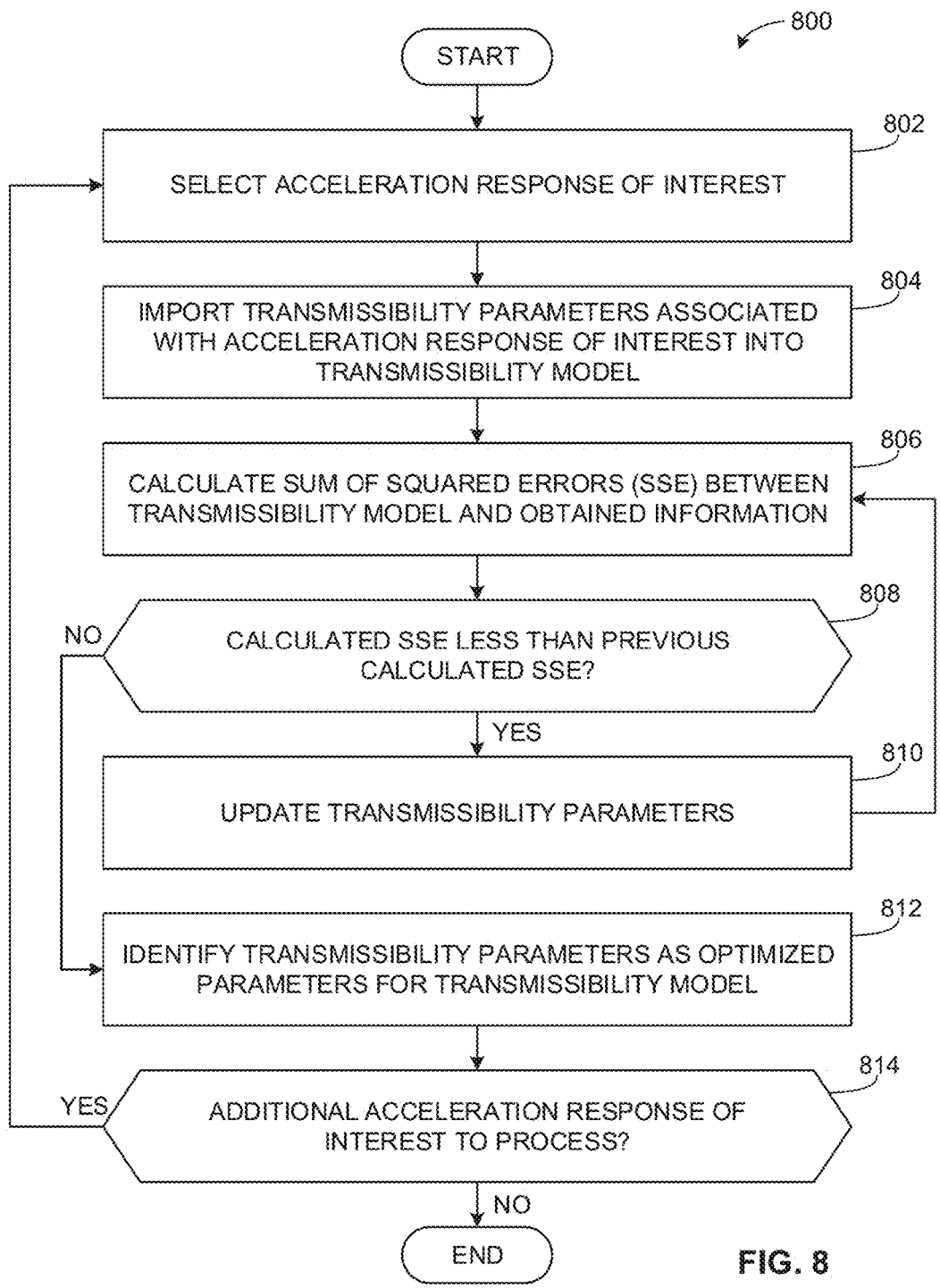

Additional detail in connection with optimizing the transmissibility response parameters (FIG. 4 block 412) is shown in FIG. 8. FIG. 8 is a flowchart representative of an example method 800 that may be executed by the example structural condition monitor apparatus 100 of FIG. 2 to optimize the transmissibility model parameters calculated by FIG. 4 block 410 for the transmissibility model used to characterize the field device 104. The example method 800 begins at block 802 when the example structural condition monitor apparatus 100 selects an acceleration response of interest to process. At block 804, the example structural condition monitor apparatus 100 imports transmissibility parameters associated with the selected acceleration response of interest from the storage database 210 into the transmissibility model. For example, the structural condition monitor apparatus 100 may import one or more calculated transmissibility model parameters associated with the selected acceleration response of interest such as, for example, the amplitude, the damping ratio, the natural frequency, the transmissibility, the vertical shift etc. Into example Equation (1) described above. The imported calculated transmissibility model parameters may be the initial set points for an optimization process described in further detail below.

At block 806, the example structural condition monitor apparatus 100 calculates a sum of squared errors (SSE) between the transmissibility model and the obtained information and stores the value in the storage database 210. In some examples, the SSE is the sum of the squares of differences predicted from collected and/or obtained values of data. For example, the structural condition monitor apparatus 100 may use example Equation (6) below to calculate the SSE prediction.

SSE=Σ((obtained information)−(transmissibility model information))²      Equation (6)

In the illustrated example of Equation (6) above, the SSE is calculated by taking the sum of the squared differences between the transmissibility parameters calculated from the obtained acceleration information and the transmissibility parameters calculated from the transmissibility model.

At block 808, the example structural condition monitor apparatus 100 determines if the calculated SSE is less than the SSE stored in the storage database 210. If, at block 808, the example structural condition monitor apparatus 100 determines that the calculated SSE is less than the previously calculated SSE stored in the storage database 210, then, at block 810, the structural condition monitor apparatus 100 updates (e.g., replaces) the transmissibility parameters utilized in example Equation (6) above, and control proceeds to block 806 to re-calculate the SSE. If, at block 808, the example structural condition monitor apparatus 100 determines that the calculated SSE is not less than the previously calculated SSE stored in the storage database 210, control proceeds to block 812 to identify the transmissibility parameters as the optimized parameters for the transmissibility model for the structure.

At block 812, the example structural condition monitor apparatus 100 identifies the transmissibility parameters utilized to calculate the minimized SSE as the optimized parameters for the transmissibility model used to characterize the structure. In some examples, one or more parameters may be calculated using the transmissibility model with optimized parameters. For example, the quality factor may be calculated by determining the maximum transmissibility value for the transmissibility model. In another example, the bandwidth may be calculated using example Equation (7) below.

$$BW = A\frac{f_n}{Q}$$

Equation (7)

In the illustrated example of Equation (7) above, the variable "BW" represents the bandwidth, the variable "A" represents the amplitude, and the variables "$f_n$" and "Q" represent the natural frequency and the quality factor, respectively. In some instances, the bandwidth is used to calculate the half power frequencies. For example, the half power frequencies may be determined to be the frequencies at which the natural frequency is increased or diminished by half the bandwidth.

The half power magnitudes may also be calculated by applying the optimized parameters and calculated half power frequencies to the transmissibility model. At block 814, the example structural condition monitor apparatus 100 determines if there is an additional acceleration response of interest to process. If, at block 814, the example structural condition monitor apparatus 100 determines there is an additional acceleration response of interest, control proceeds to block 802 to select an additional acceleration response of interest, otherwise the example method 800 concludes.

Figure 9:
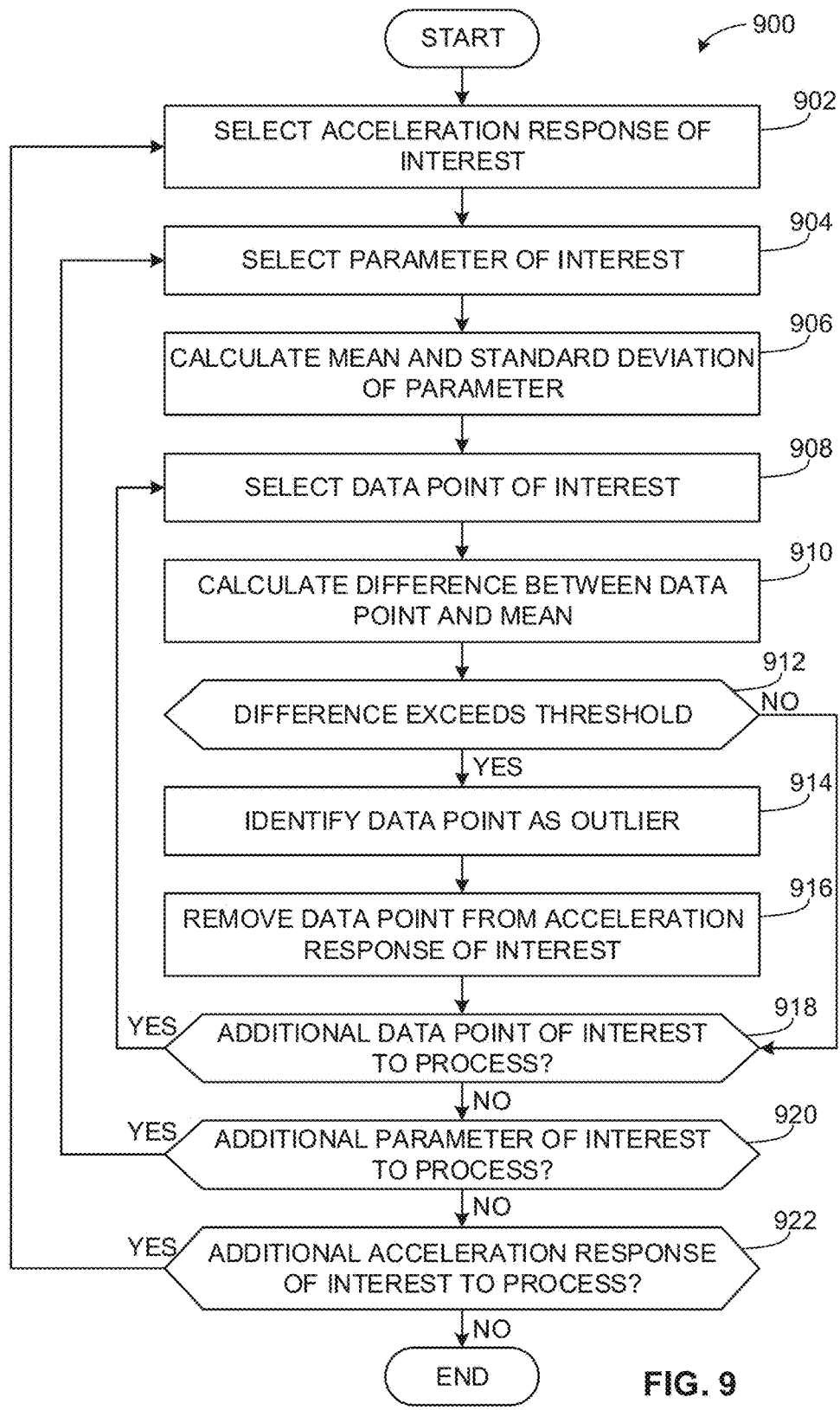

Additional detail in connection with identifying outliers (FIG. 4 block 418) is shown in FIG. 9. FIG. 9 is a flowchart representative of an example method 900 that may be executed by the example structural condition monitor apparatus 100 of FIG. 2 to identify outliers in the generated transmissibility models used to characterize the structure. For example, the structure may be the field device 104. The example method 900 begins at block 902 when the example structural condition monitor apparatus 100 selects an acceleration response of interest to process. At block 904, the example structural condition monitor apparatus 100 selects a parameter of interest (e.g., a transmissibility parameter of interest) to process. At block 906, the example structural condition monitor apparatus 100 calculates at least the mean and standard deviation of the selected parameter for the selected acceleration response of interest. At block 908, example structural condition monitor apparatus 100 selects a data point of interest. At block 910, the example structural condition monitor apparatus 100 calculates a difference between the data point and the mean.

At block 912, the example structural condition monitor apparatus 100 determines if the difference satisfies a threshold. In some examples, the threshold is determined by user input. In some instances, the threshold is one or more standard deviations of the calculated mean of the selected parameter. If, at block 912, the example structural condition monitor apparatus 100 determines the difference does not exceed the threshold, control proceeds to block 918 to determine if there is an additional data point of interest to process. If, at block 912, the example structural condition monitor apparatus 100 determines the difference exceeds the threshold then, at block 914, the structural condition monitor apparatus 100 identifies the data point as an outlier. At block 916, the example structural condition monitor apparatus 100 removes the data point from the acceleration response of interest. In some examples, the data point is stored in the storage database 210 for potential further analysis. For example, the identified data point or a plurality of identified data points may be analyzed to determine if the acceleration response of interest is not a candidate to use for generating one or more vibration models.

At block 918, the example structural condition monitor apparatus 100 determines if there is an additional data point to process. If, at block 918, the example structural condition monitor apparatus 100 determines there is an additional data point to process, control proceeds to block 908 to select an additional data point of interest. If, at block 918, the example structural condition monitor apparatus 100 determines there is not an additional data point of interest to process then, at block 920, the structural condition monitor apparatus 100 determines if there is an additional parameter of interest to process. If, at block 920, the example structural condition monitor apparatus 100 determines there is an additional parameter of interest to process, control proceeds to block 904 to select an additional parameter of interest. If, at block 920, the example structural condition monitor apparatus 100 determines there is not an additional parameter of interest to process then, at block 922, the example structural condition monitor apparatus 100 determines if there is an additional acceleration response of interest to process. If, at block 922, the example structural condition monitor apparatus 100 determines there is an additional acceleration response of interest to process, control proceeds to block 902 to select an additional acceleration response of interest to process, otherwise the example method 900 concludes.

Figure 10:
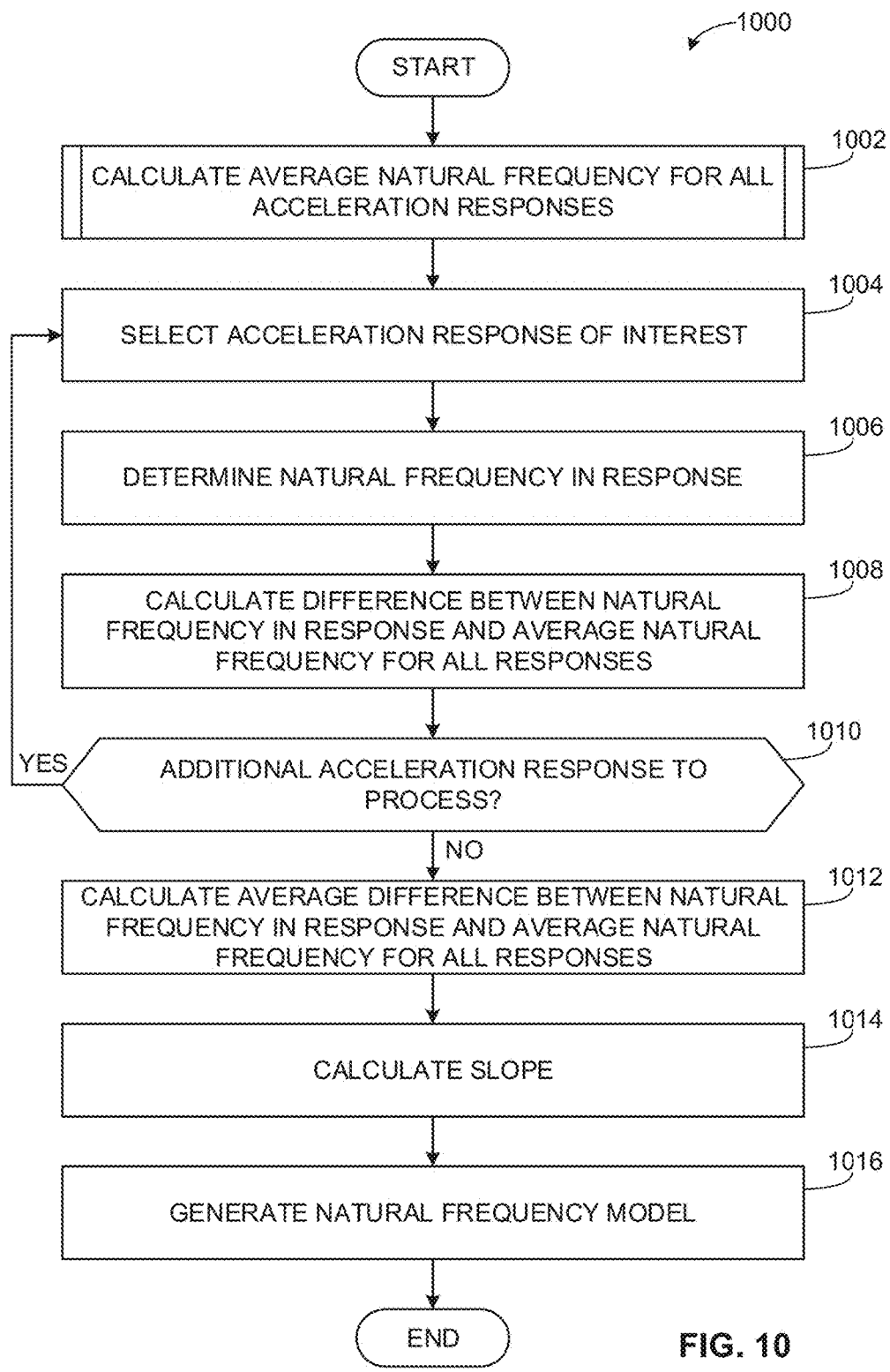

Additional detail in connection with generating the natural frequency model (FIG. 3 block 306) is shown in FIG. 10. FIG. 10 is a flowchart representative of an example method 1000 that may be performed by the example structural condition monitor apparatus 100 of FIG. 2 to generate the natural frequency model used to characterize the structure. The example method 1000 begins at block 1002 when the example structural condition monitor apparatus 100 calculates the average natural frequency for one or more acceleration responses. At block 1004, the example structural condition monitor apparatus 100 selects an acceleration response of interest to process. At block 1006, the example structural condition monitor apparatus 100 determines the natural frequency of the acceleration response. In some examples, the example structural condition monitor apparatus 100 calculates the natural frequency using the example method 700 at block 708 (FIG. 7 block 708). In some instances, the example structural condition monitor apparatus 100 identifies the natural frequency of the acceleration response by querying the storage database 210. At block 1008, the example structural condition monitor apparatus 100 calculates a difference between the determined natural frequency in the acceleration response and the calculated average natural frequency.

At block 1010, the example structural condition monitor apparatus 100 determines if there is an additional acceleration response of interest to process. If, at block 1010, the example structural condition monitor apparatus 100 determines that there is an additional acceleration response of interest to process, control proceeds to block 1004 to select an additional acceleration response of interest. If, at block 1010, the example structural condition monitor apparatus 100 determines that there is not an additional acceleration response of interest to process, then, at block 1012, the structural condition monitor apparatus 100 calculates an average of the calculated differences between the determined natural frequencies in the selected responses and the calculated average natural frequency. At block 1014, the example structural condition monitor apparatus 100 calculates a slope of a linear fit for the natural frequency model. For example, the slope may be calculated as a ratio of the calculated average difference and a total number of acceleration responses analyzed by the example method 1000.

In the illustrated example of FIG. 10, at block 1016, the example structural condition monitor apparatus 100 generates the natural frequency model. For example, the structural condition monitor apparatus 100 may use example Equation (8) below to generate the natural frequency model.

$$f_{n_{linear\,fit}} = m*N + f_{n_{average}} \quad \text{Equation (8)}$$

In the illustrated example of Equation (8) above, the variable "$f_{n_{linear\,fit}}$" is the natural frequency calculated by the natural frequency model. The variable "m" is the slope and the variable "$f_{n_{average}}$" is the calculated average natural frequency for one or more acceleration responses. The variable "N" is a number of operating cycles experienced by the field device 104. The number of operating cycles may be based on a period of time (e.g., a period of 100 milliseconds), a number of actions performed by the field device 104 (e.g., a number of times the valve 110 opens), etc.

Figure 11:
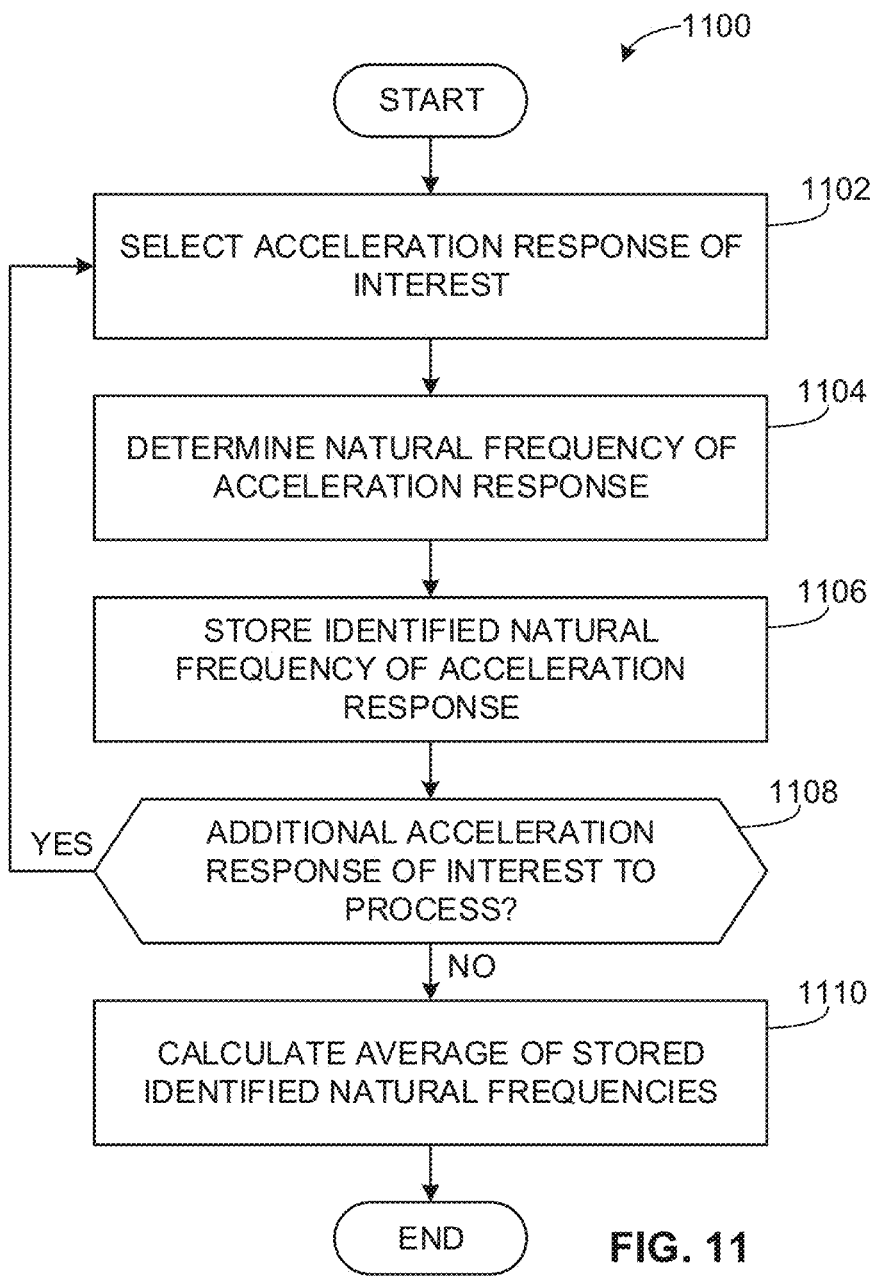

Additional detail in connection with calculating the average natural frequency for one or more acceleration responses (FIG. 10 block 1002) is shown in FIG. 11. FIG. 11 is a flowchart representative of an example method 1100 that may be performed by the example structural condition monitor apparatus 100 of FIG. 2 to calculate an average natural frequency of structure. The example method 1100 begins at block 1102 when the example structural condition monitor apparatus 100 selects an acceleration response of interest. At block 1104, the example structural condition monitor apparatus 100 determines the natural frequency in the selected acceleration response. At block 1106, the example structural condition monitor apparatus 100 stores the determined natural frequency of the acceleration response in the storage database 210. At block 1108, the example structural condition monitor apparatus 100 deter mines if there is an additional acceleration response of interest to process. If, at block 1108, the example structural condition monitor apparatus 100 determines there is an additional acceleration response of interest to process, control proceeds to block 1102 to select an additional acceleration response of interest. If, at block 1108, the example structural condition monitor apparatus 100 determines that there is not an additional acceleration response of interest to process then, at block 1110, the example structural condition monitor apparatus 100 calculates the average of the stored determined natural frequencies for the selected acceleration responses.

Figure 12:
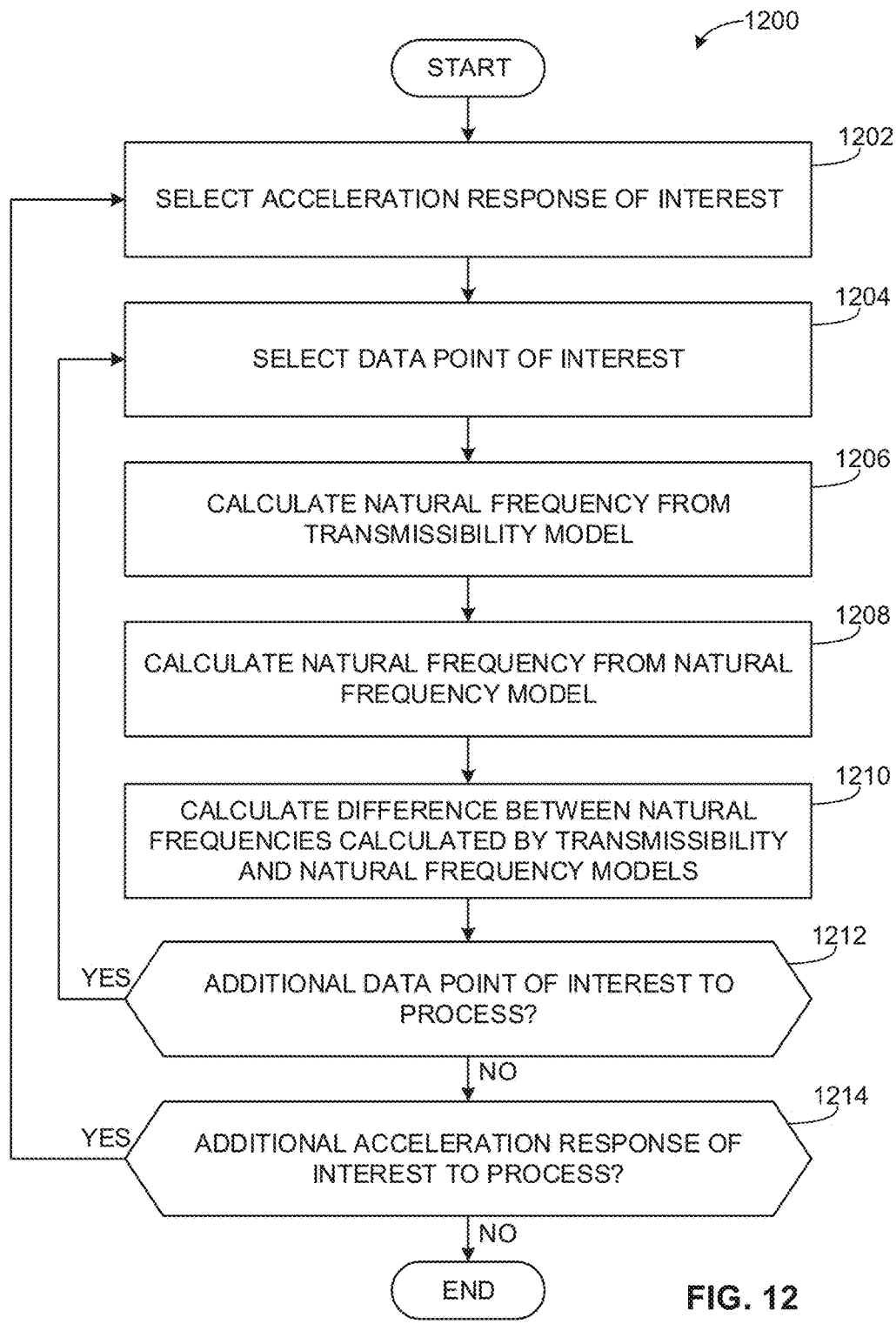

Additional detail in connection with calculating the natural frequency difference (FIG. 3 block 310) is shown in FIG. 12. FIG. 12 is a flowchart representative of an example method 1200 that may be performed by the example structural condition monitor apparatus 100 of FIG. 2 to calculate a difference between the natural frequencies calculated by the transmissibility and natural frequency models of the structure. The example method 1200 begins at block 1202 when the example structural condition monitor apparatus 100 selects an acceleration response of interest. At block 1204, the example structural condition monitor apparatus 100 selects a data point of interest. In some examples, the data point may be the most recently obtained and processed data point by the example structural condition monitor apparatus 100. For example, the data point may be the first data point in a first-in first-out (FIFO) buffer queue that was processed by the example structural condition monitor apparatus 100 and obtained by the vibration sensing devices 116,118 during a time period in which the field device 104 was experiencing extreme vibration.

At block 1206, the example structural condition monitor apparatus 100 calculates the natural frequency of the structure by entering the obtained acceleration information into the transmissibility model. For example, the structural condition monitor apparatus 100 may enter the obtained acceleration information into the transmissibility model to calculate the natural frequency of the field device 104. At block 1208, the example structural condition monitor apparatus 100 calculates the natural frequency of the structure by entering the obtained acceleration information into the natural frequency model. For example, the structural condition monitor apparatus 100 may enter the calculated number of operating cycles into the natural frequency model to calculate the baseline (e.g., expected) natural frequency of the field device 104 at that specific number of operating cycles.

At block 1210, the example structural condition monitor apparatus 100 calculates a difference between the natural frequency calculated by the transmissibility model and the natural frequency calculated by the natural frequency model. In some examples, the difference may be an absolute value difference. At block 1212, the example structural condition monitor apparatus 100 determines if there is an additional data point of interest to process. If, at block 1212, the example structural condition monitor apparatus 100 deter refines that there is an additional data point of interest to process, control proceeds to block 1204 to select an additional data point of interest to process. If, at block 1212, the example structural condition monitor apparatus 100 determines that there is not an additional data point of interest to process, then, at block 1214, the structural condition monitor apparatus 100 determines if there is an additional acceleration response of interest to process. If, at block 1214, the example structural condition monitor apparatus 100 determines that there is an additional acceleration response of interest to process, control proceeds to block 1202 to select an additional acceleration response of interest, otherwise the example method 1200 concludes.

Figure 13:
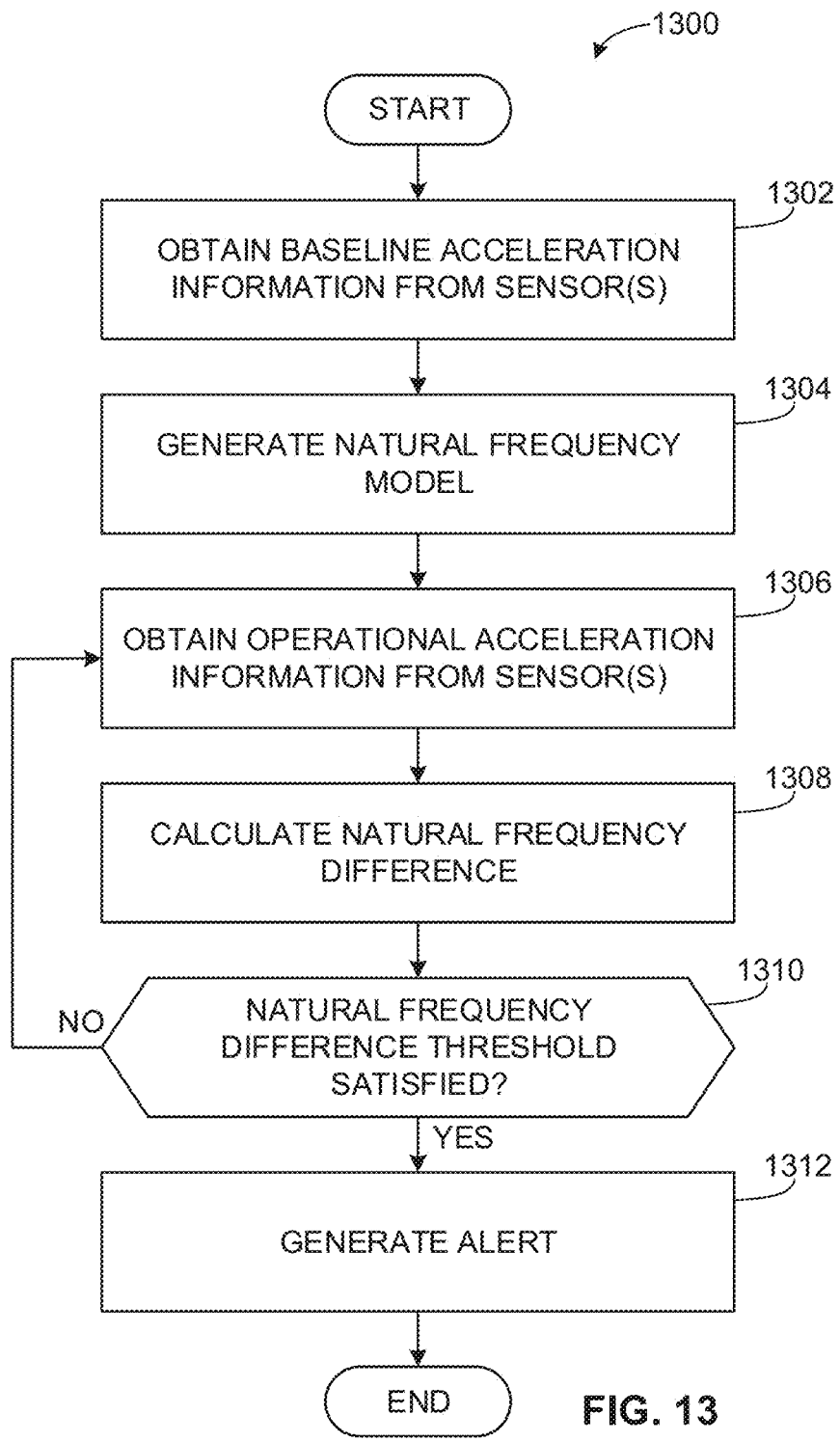

FIG. 13 is a flowchart representative of an example method 1300 that may be executed by the example structural condition monitor apparatus 100 of FIG. 2 to identify the condition of the structure without the transmissibility model. For example, the structure may be the field device 104 and the condition of the structure may be the condition of the pneumatic tube connection 112 (e.g., the pneumatic tube connection 112 is decoupling). In some examples, the example structural condition monitor apparatus 100 may obtain acceleration information from only one acceleration sensor. In those examples, the structural condition monitor apparatus would be unable to calculate a transmissibility ratio. In some instances, it may be beneficial to reduce power consumption and/or processor requirements by not using the transmissibility model. For example, the structural condition monitor apparatus 100 may obtain acceleration information from one or more vibration sensing devices (e.g., the vibration sensing device 116, the vibration sensing device 118, etc.). The example structural condition monitor apparatus 100 may generate one or more vibration models that includes at least the natural frequency model.

In the illustrated example of FIG. 13, the example method 1300 begins at block 1302 when the example structural condition monitor apparatus 100 obtains baseline acceleration information from one or more vibration sensing devices (e.g., the vibration sensing device 116, the vibration sensing device 118, etc.) during a time period of known good health for the structure. For example, the structural condition a monitor apparatus 100 may obtain acceleration information from the vibration sensing device 116 coupled to the field device 104 in a time period in which the field device 104 is in known good health. At block 1304, the example structural condition monitor apparatus 100 generates the natural frequency model. In some examples, the example structural condition monitor apparatus 100 may generate the natural frequency model in accordance with the example method 1000.

At block 1306, the example structural condition monitor apparatus 100 obtains acceleration information from one or more acceleration sensors during operation. At block 1308, the example structural condition monitor apparatus 100 calculates the difference between the calculated natural frequency of the structure and the calculated natural frequency from the natural frequency model. For example, the structural condition monitor apparatus 100 may calculate the natural frequency by determining the midpoint between the frequencies corresponding to the maximum and minimum transmissibility. At block 1310, the example structural condition monitor apparatus 100 determines if the natural frequency difference satisfies a threshold. If, at block 1310, the example structural condition monitor apparatus 100 determines that the difference does not satisfy the threshold, control proceeds to block 1306 to obtain additional operational acceleration information at block 1310, the example structural condition monitor apparatus 100 determines that the difference satisfies the threshold, then, at block 1312, the example structural condition monitor apparatus 100 generates an alert. For example, the alert may be a text-based alarm in a process control software indicating that the pneumatic tube connection 112 is decoupling from the field device 104.

Figure 14:
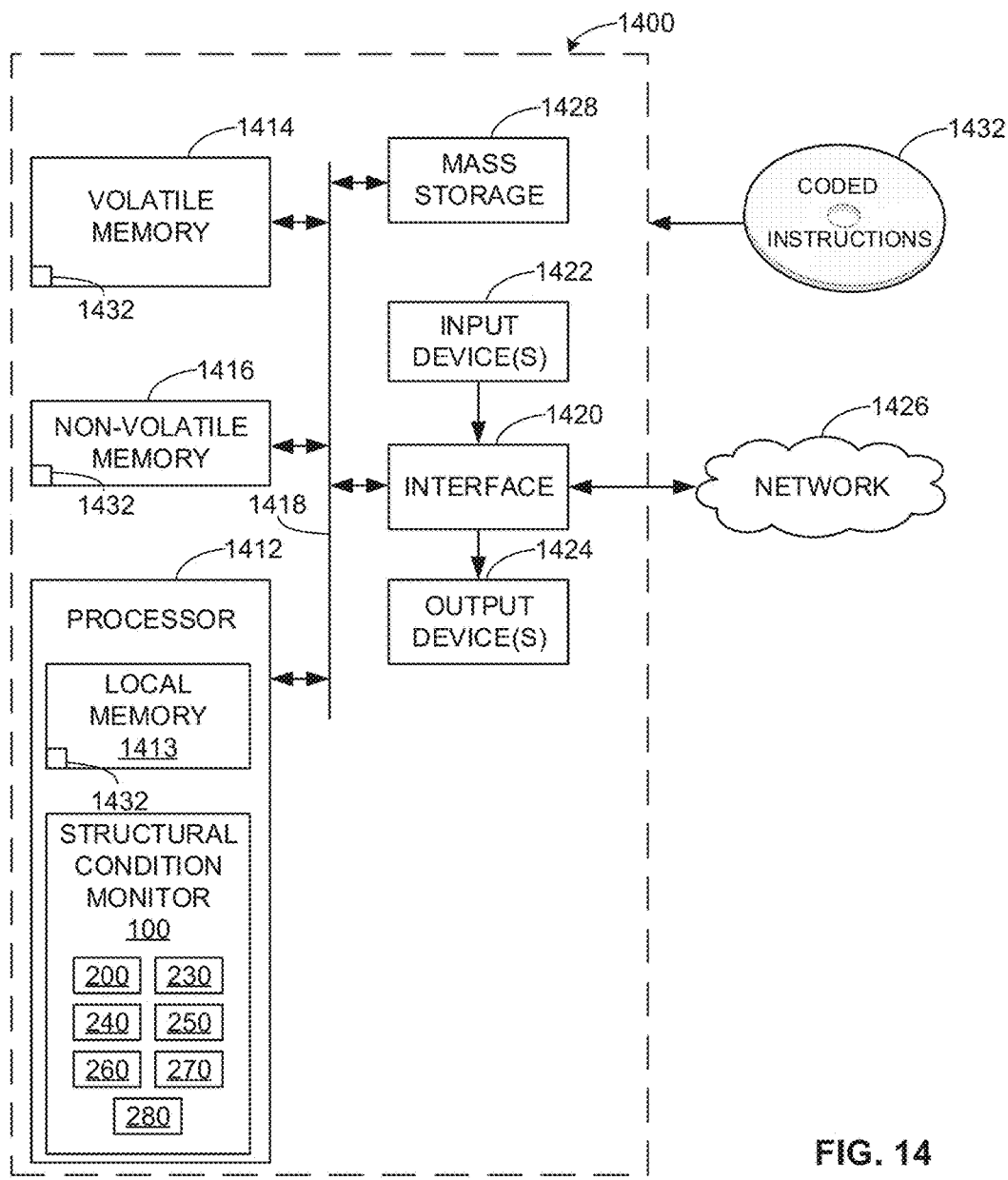
FIG. 14 is a block diagram of an example processor platform structured to execute machine readable instructions to implement the methods of FIGS. 3-13 and the example structural condition monitor of FIGS. 1 and 2.

FIG. 14 is a block diagram of an example processor platform 1400 capable of executing instructions to implement the methods of FIGS. 3-13 and the apparatus of FIG. 2. The processor platform 1400 can be, for example, a server, a personal computer, a process control system controller, a computing device of a process control system or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors or controllers from any desired family or manufacturer.

The processor 1412 of the illustrated example includes a local memory 1413 (e.g., a cache) and the example structural condition monitor apparatus 100 comprising the example collection engine 200, the example transmissibility model generator 230, the example natural frequency model generator 240, the example transmissibility model calculator 250, the example natural frequency model calculator 260, the example natural frequency difference calculator 270, and the alert generator 280. The processor 1412 of the illustrated example executes the instructions to implement the example structural condition monitor apparatus 100, comprising the example collection engine 200, the example transmissibility model generator 230, the example natural frequency model generator 240, the example transmissibility model calculator 250, the example natural frequency model calculator 260, the example natural frequency difference calculator 270, and the alert generator 280. The processor 1412 of the illustrated example is in communication with a main memory including a volatile memory 1414 and a non-volatile memory 1416 via a bus 1418.

The volatile memory 1414 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1416 may be implemented by flash memory and/or any other desired type of memory device. Access to the main memory 1414,1416 is controlled by a memory controller.

The processor platform 1400 of the illustrated example also includes an interface circuit 1420. The interface circuit 1420 may be implemented by any type of interface standard, such as an Ethernet interface, a universal serial bus (USB), and/or a PCI express interface. The example bus 1418 and the example interface circuit 1420 implements the example storage database interface 220.

In the illustrated example, one or more input devices 1422 are connected to the interface circuit 1420. The input device(s) 1422 permit(s) a user to enter data and commands into the processor 1412. The input device(s) can be implemented by, for example, an audio sensor, a microphone, a camera (still or video), a keyboard, a button, a mouse, a touchscreen, a track-pad, a trackball, isopoint and/or a voice recognition system One or more output devices 1424 are also connected to the interface circuit 1420 of the illustrated example. The output devices 1424 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1420 of the illustrated example, thus, typically includes a graphics driver card, a graphics driver chip or a graphics driver processor.

The interface circuit 1420 of the illustrated example also includes a communication device such as a transmitter, a receiver, a transceiver, a modem and/or network interface card to facilitate exchange of data with external machines (e.g., computing devices of any kind) via a network 1426 (e.g., an Ethernet connection, a digital subscriber line (DSL), a telephone line, coaxial cable, a cellular telephone system, etc.).

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and digital versatile disk (DVD) drives. The example mass storage 1428 implements the example storage database 210.

Coded instructions 1432 to implement the methods of FIGS. 3-13 may be stored in the mass storage device 1428, in the volatile memory 1414, in the non-volatile memory 1416, and/or on a removable tangible computer-readable storage medium such as a CD or DVD.

From the foregoing, it will be appreciated that the above disclosed structural condition monitor apparatus and methods provide prognostic health monitoring of a structure to monitor for a condition of the structure. As a result, the operating lifecycle of the structure can be optimized by operating the structure until the condition of the structure has been identified and avoid a premature replacement of the structure. Also, the identification of the condition of the structure generates an alert to personnel to allow the performance of preventative maintenance and/or replacement of the structure prior to a potential failure that may produce unwanted downtime in a process control environment.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
an operational collection engine to measure first operational acceleration information from a first sensor installed at a first location and second operational acceleration information from a second sensor installed at a second location on a structure;
a first vibration model response calculator to calculate a first vibration model response by entering the measured first and second operational acceleration information into a first vibration model, the first vibration model response including a first natural frequency, the first natural frequency to be calculated by determining a transmissibility based on a ratio of the first operational acceleration information and the second operational acceleration information;

a second vibration model response calculator to calculate a second vibration model response by entering a calculated number of operating cycles into a second vibration model, the second vibration model response including a second natural frequency, the second vibration model to be generated by:

determining an average natural frequency based on natural frequencies associated with acceleration responses measured by the first sensor and the second sensor; and determining an average natural frequency difference based on an average of differences between the average natural frequency and the natural frequencies associated with the acceleration responses; and an alert generator to generate an alert to identify a condition of the structure based on a difference between the first vibration model response and the second vibration model response.

2. The apparatus of claim 1, further including:

a baseline collection engine to measure first baseline acceleration information from the first sensor and second baseline acceleration information from the second sensor;

a transmissibility model generator to generate the first vibration model for the structure; and a natural frequency model generator to generate the second vibration model for the structure.

3. The apparatus of claim 2, wherein the transmissibility model generator is configured to generate the first vibration model for the structure by performing a curve fit for calculated transmissibility information, the calculated transmissibility information based on the first baseline acceleration information and the second baseline acceleration information.

4. The apparatus of claim 2, wherein the natural frequency model generator is configured to generate the second vibration model for the structure by:

determining calculated natural frequency information based on the first baseline acceleration information and the second baseline acceleration information, the calculated natural frequency information including the average natural frequency and the average natural frequency difference;

determining a slope based on a ratio of the average natural frequency difference and a first quantity of the acceleration responses; and performing a linear curve fit for the calculated natural frequency information, the linear curve fit based on a sum of (1) the average natural frequency and (2) a multiplication of a second quantity of operating cycles and the slope.

5. The apparatus of claim 1, wherein the alert generator is configured to identify the condition of the structure when a difference between the first natural frequency and the second natural frequency satisfies a threshold.

6. The apparatus of claim 1, wherein the condition of the structure is a degradation of the structure.

7. A method comprising:

measuring first operational acceleration information from a first sensor installed at a first location and second operational acceleration information from a second sensor installed at a second location on a structure;

calculating a first vibration model response by entering the measured first and second operational acceleration information into a first vibration model, the first vibration model response including a first natural frequency, the first natural frequency to be calculated by determining a transmissibility based on a ratio of the first operational acceleration information and the second operational acceleration information;

calculating a second vibration model response by entering a calculated number of operating cycles into a second vibration model, the second vibration model response including a second natural frequency, the second vibration model to be generated by:

determining an average natural frequency based on natural frequencies associated with acceleration responses measured by the first sensor and the second sensor; and determining an average natural frequency difference based on an average of differences between the average natural frequency and the natural frequencies associated with the acceleration responses; and identifying a condition of the structure based on a difference between the first vibration model response and the second vibration model response.

8. The method of claim 7, further including:

measuring first baseline acceleration information from the first sensor and second baseline acceleration information from the second sensor; and generating the first vibration model and the second vibration model for the structure based on the baseline acceleration information measured by the sensors.

9. The method of claim 8, wherein generating the first vibration model includes performing a curve fit for calculated transmissibility information, the calculated transmissibility information based on the first baseline acceleration information and the second baseline acceleration information.

10. The method of claim 8, wherein generating the second vibration model includes:

determining calculated natural frequency information based on the first baseline acceleration information and the second baseline acceleration information, the calculated natural frequency information including the average natural frequency and the average natural frequency difference;

determining a slope based on a ratio of the average natural frequency difference and a first quantity of the acceleration responses; and performing a linear curve fit for the calculated natural frequency information, the linear curve fit based on a sum of (1) the average natural frequency and (2) a multiplication of a second quantity of operating cycles and the slope.

11. The method of claim 8, wherein the determining of the difference between the first vibration model response and the second vibration model response includes determining a difference between the first natural frequency and the second natural frequency.

12. The method of claim 11, wherein the identifying the condition of the structure based on the difference between the first vibration model response and the second vibration model response includes determining when the difference between the first and second natural frequencies satisfies a threshold.

13. A tangible computer-readable storage medium comprising instructions which, when executed, cause a machine to at least:

measure first operational acceleration information from a first sensor installed at a first location and second operational acceleration information from a second sensor installed at a second location on a structure;

calculate a first vibration model response by entering the measured first and second operational acceleration information into a first vibration model, the first vibration model response including a first natural frequency, the first natural frequency to be calculated by determining a transmissibility based on a ratio of the first operational acceleration information and the second operational acceleration information;

calculate a second vibration model response by entering a calculated number of operating cycles into a second vibration model, the second vibration model response including a second natural frequency, the second vibration model to be generated by:

determining an average natural frequency based on natural frequencies associated with acceleration responses measured by the first sensor and the second sensor; and determining an average natural frequency difference based on an average of differences between the average natural frequency and the natural frequencies associated with the acceleration responses; and identify a condition of the structure based on a difference between the first vibration model response and the second vibration model response.

14. The tangible computer-readable storage medium of claim 13, wherein the instructions, when executed, cause the machine to:

measure first baseline acceleration information from the first sensor installed at the first location and second baseline acceleration information from the second sensor installed at the second location on the structure; and generate the first vibration model and the second vibration model for the structure based on the baseline acceleration information measured by the sensors.

15. The tangible computer-readable storage medium of claim 14, wherein the instructions, when executed, cause the machine to generate the first vibration model by performing a curve fit for calculated transmissibility information, the calculated transmissibility information based on the first baseline acceleration information and the second baseline acceleration information.

16. The tangible computer-readable storage medium of claim 14, wherein the instructions, when executed, cause the machine to generate the second vibration model by:

determining calculated natural frequency information based on the first baseline acceleration information and the second baseline acceleration information, the calculated natural frequency information including the average natural frequency and the average natural frequency difference;

determining a slope based on a ratio of the average natural frequency difference and a first quantity of the acceleration responses; and performing a linear curve fit for the calculated natural frequency information, the linear curve fit based on a sum of (1) the average natural frequency and (2) a multiplication of a second quantity of operating cycles and the slope.

17. The tangible computer-readable storage medium of claim 13, wherein the instructions, when executed, cause the machine to determine the difference between the first vibration model response and the second vibration model response by determining a difference between the first natural frequency and the second natural frequency.

18. The tangible computer-readable storage medium of claim 17, wherein the instructions, when executed, cause the machine to identify the condition of the structure based on the difference between the first vibration model response and the second vibration model response by determining when the difference between the first and second natural frequencies satisfies a threshold.

19. The apparatus of claim 1, wherein the structure is an actuator, a valve, or a field device.

20. The apparatus of claim 1, wherein at least one of the first sensor or the second sensor is an accelerator sensor, a motion sensor, or a vibration sensor.

* * * * *